United States Patent
Sterk et al.

(10) Patent No.: US 8,765,668 B2
(45) Date of Patent: Jul. 1, 2014

(54) METHODS OF SYNTHESIS OF β-AMINOBUTYRYL SUBSTITUTED COMPOUNDS

(75) Inventors: Damjan Sterk, Ljubljana (SI); Matjaz Ustar, Ljubljana (SI); Marko Zlicar, Ljubljana (SI)

(73) Assignee: Lek Pharmaceuticals D.D., Ljubjiana (SI)

(*) Notice: Subject to any disclaimer, the term of this patent is extended or adjusted under 35 U.S.C. 154(b) by 0 days.

(21) Appl. No.: 13/702,050

(22) PCT Filed: Jun. 3, 2011

(86) PCT No.: PCT/EP2011/059198
§ 371 (c)(1),
(2), (4) Date: Jan. 23, 2013

(87) PCT Pub. No.: WO2011/151443
PCT Pub. Date: Dec. 8, 2011

(65) Prior Publication Data
US 2013/0130974 A1  May 23, 2013

(30) Foreign Application Priority Data

Jun. 4, 2010  (EP) .................................... 10164933
Jan. 12, 2011 (EP) .................................... 11150740
Jun. 2, 2011  (EP) .................................... 11168582

(51) Int. Cl.
*A61K 38/28* (2006.01)
*A61P 5/50* (2006.01)
*A61K 38/26* (2006.01)
*A61P 3/10* (2006.01)
*A61P 7/12* (2006.01)
*C07K 14/605* (2006.01)
*A01N 43/58* (2006.01)
*A01N 43/60* (2006.01)
*A61K 31/50* (2006.01)
*A61K 31/495* (2006.01)
*C07D 491/00* (2006.01)
*C07D 495/00* (2006.01)
*C07D 497/00* (2006.01)

(52) U.S. Cl.
USPC .......... 514/6.5; 514/11.7; 514/249; 544/350; 435/119

(58) Field of Classification Search
None
See application file for complete search history.

(56) References Cited

FOREIGN PATENT DOCUMENTS

| EP | 2392575 A1 | * | 12/2011 |
| WO | WO 03/004498 A1 | | 1/2003 |
| WO | WO 03004498 A1 | * | 1/2003 |
| WO | WO 2008/040974 A1 | | 4/2008 |
| WO | WO 2008040974 A1 | * | 4/2008 |

OTHER PUBLICATIONS

Preetz A., et al.: "Binap: rhodium-diolefin complexes in asymmetric hydrogenation," Tetrajedrpm Asymmetry, Pergamon Press Ltd., Oxford, GB. vol. 21, No. 9-10, May 17, 2010, pp. 1226-1231, XP027185334. ISSN: 0957-4166 [retrieved on May 12, 2010].

Mühlstädt M, et al.: "Nitrovinylcarbonsäureester durch Kondensation von w-Nitrocarbonsäureestern mit aromatischen Aldehyden," Journal Für Praktische Chemie, vol. 317, No. 6, 1975, pp. 919-925 XP002606286, the whole document; in particular, p. 920, the preparation of compounds 6d and 61.

* cited by examiner

*Primary Examiner* — James H Alstrum Acevedo
*Assistant Examiner* — Zachary J Miknis
(74) *Attorney, Agent, or Firm* — Arent Fox LLP

(57) ABSTRACT

The present invention relates to process to prepare β-aminobutyryl compounds having β-amino acid core structural moieties and optionally having γ-phenyl and/or heterocyclic structural moieties. Such compounds are useful as key structure framework of modern drug chemistry.

5 Claims, No Drawings

METHODS OF SYNTHESIS OF β-AMINOBUTYRYL SUBSTITUTED COMPOUNDS

CROSS-REFERENCE TO RELATED APPLICATION

This application is a National Stage entry of international Application No. PCT/EP2011/059198, filed Jun. 3, 2011, which claims priority to European Application Nos. 10164933.3 filed Jun. 4, 2010; 11150740.6 filed Jan. 12, 2011 and 11168582.2 filed Jun. 2, 2011, the entire specifications, claims and drawings of which are incorporated herewith by reference.

FIELD OF THE INVENTION

The present invention relates to the field of organic chemistry, more specifically to β-aminobutyryl substituted compounds, in particular β-aminobutyryl compounds having γ-aryl (notably aryl) groups, and/or heterocyclic structural moieties. Such compounds are useful as key structure framework of modern drug chemistry and especially of antidiabetic agents.

BACKGROUND OF THE INVENTION

β-Amino acids are of interest in the preparation of active pharmaceutical ingredients (APIs). The β-amino acid moiety in APIs of interest is normally part of a complex whole structure. Complexity is typically enhanced when considering a chiral center at the β-position of the β-aminobutyryl group and the general desire to obtain enantiopure compounds.

A particularly interesting class of APIs having β-amino acid structural moieties are dipeptidyl peptidase-4 (DPP-4) inhibitors which act as antidiabetic agents. DPP-4 inhibitors are oral antidiabetic drugs, which reduces glucose blood levels by a new mechanism of action in which the DPP-4 inhibitors ("gliptins") inhibit inactivation of glucagon-like peptide (GLP), which stimulates insulin secretion. The benefit of these medicines lies in its lower side-effects (e.g., less hypoglycemia, less weight gain) in the control of blood glucose values. It can be used for treatment of diabetes mellitus type 2 either alone or in combination with other oral antihyperglycemic agents, such as metformin or a thiazolidinediones.

The first member of the novel pharmacological group is sitagliptin (compound of formula I), which is chemically (R)-3-amino-1-(3-(trifluoromethyl)-5,6-dihydro-[1,2,4]triazolo[4,3-a]pyrazin-7(8H)-yl)-4-(2,4,5-trifluorophenyl)butan-1-one and which structure includes a β-amino acid part.

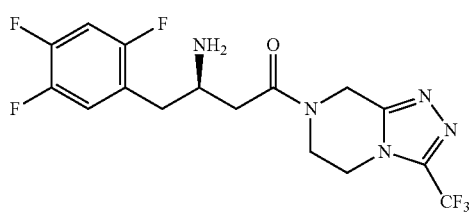

I

However, an inclusion of an β-amino acid framework into more complex molecules remains a permanent challenge for industrial production.

This is well reflected in the literature for the synthesis of sitagliptin. Several methods are described, how to introduce the β-amino acid structure into the molecule of sitagliptin. The first synthesis of sitagliptin molecule used chiral unusual dihydropyrazine chiral promoters, diazomethane and silver salts (WO 03/004498) which are unacceptable reagents for industrial synthesis—Scheme 1.

Scheme 1

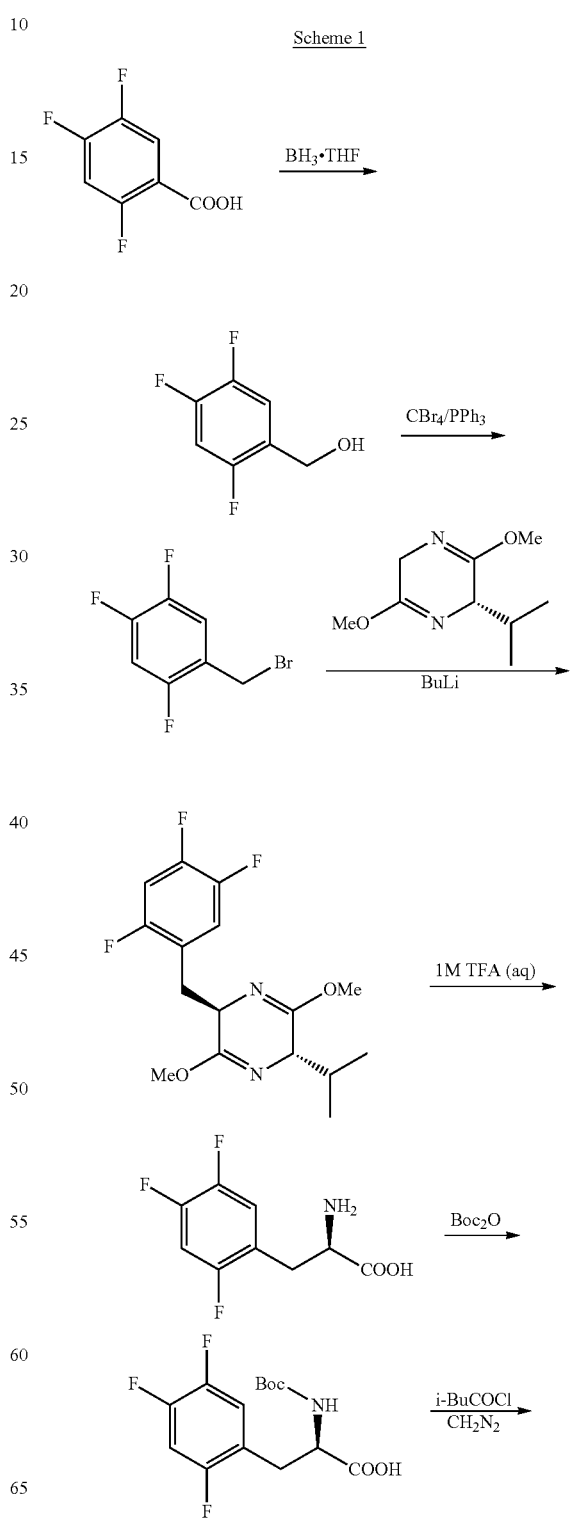

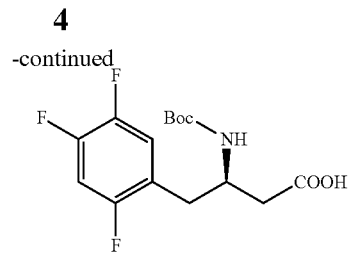

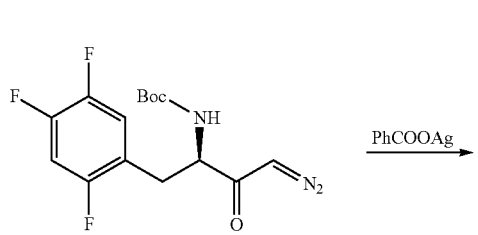

Better approaches include enantioselective hydrogenation of β-enamino acid derivatives but they need expensive precious metal catalysts, such as rhodium (WO 03/004498, Tetrahedron Asymmetry 17, 205 (2006)) or ruthenium (WO 09/064,476) and expensive ligands, such as ferrocenyl diphosphine ligands—JOSIPHOS catalysts (WO 04/085378, WO 05/097733, WO 06/081151, J. Am. Chem. Soc., 126, 9918 (2004)).

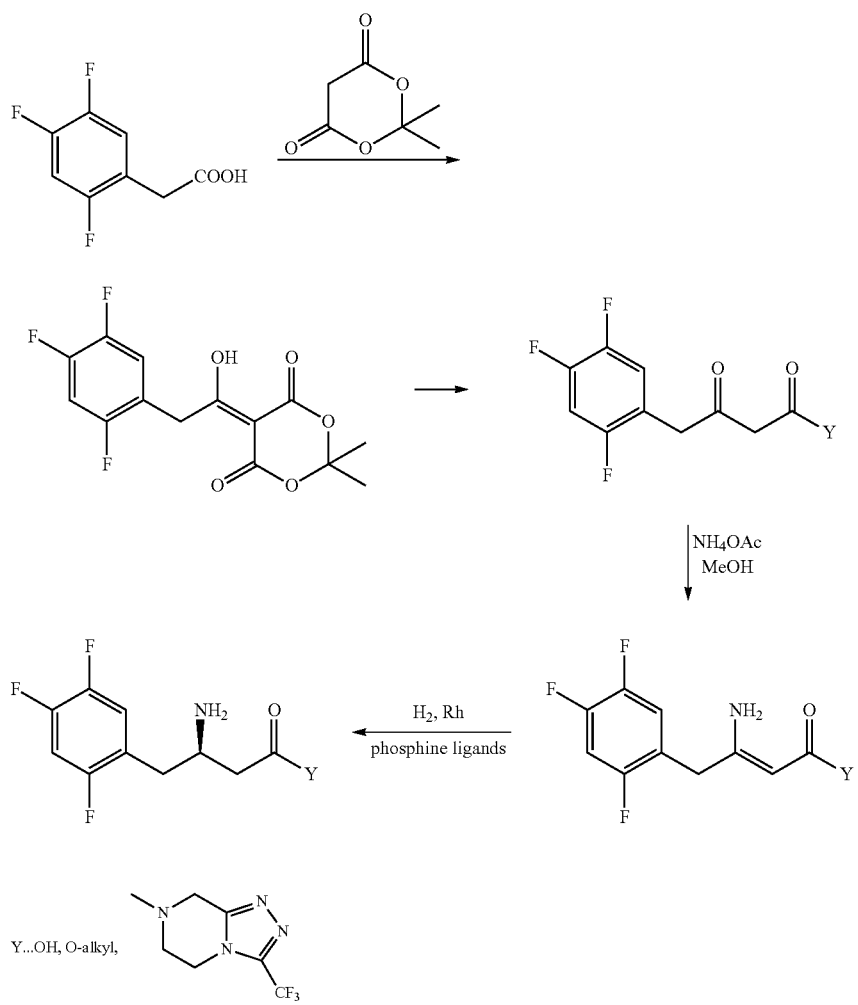

Another option is a hydrogenation with cheaper achiral catalyst, but with chiral derivatisation of enamines derived from phenylglycinamide—Scheme 3 (WO 04/085661). The obtained e.e. values are not sufficient for pharmaceutical use.

Scheme 3
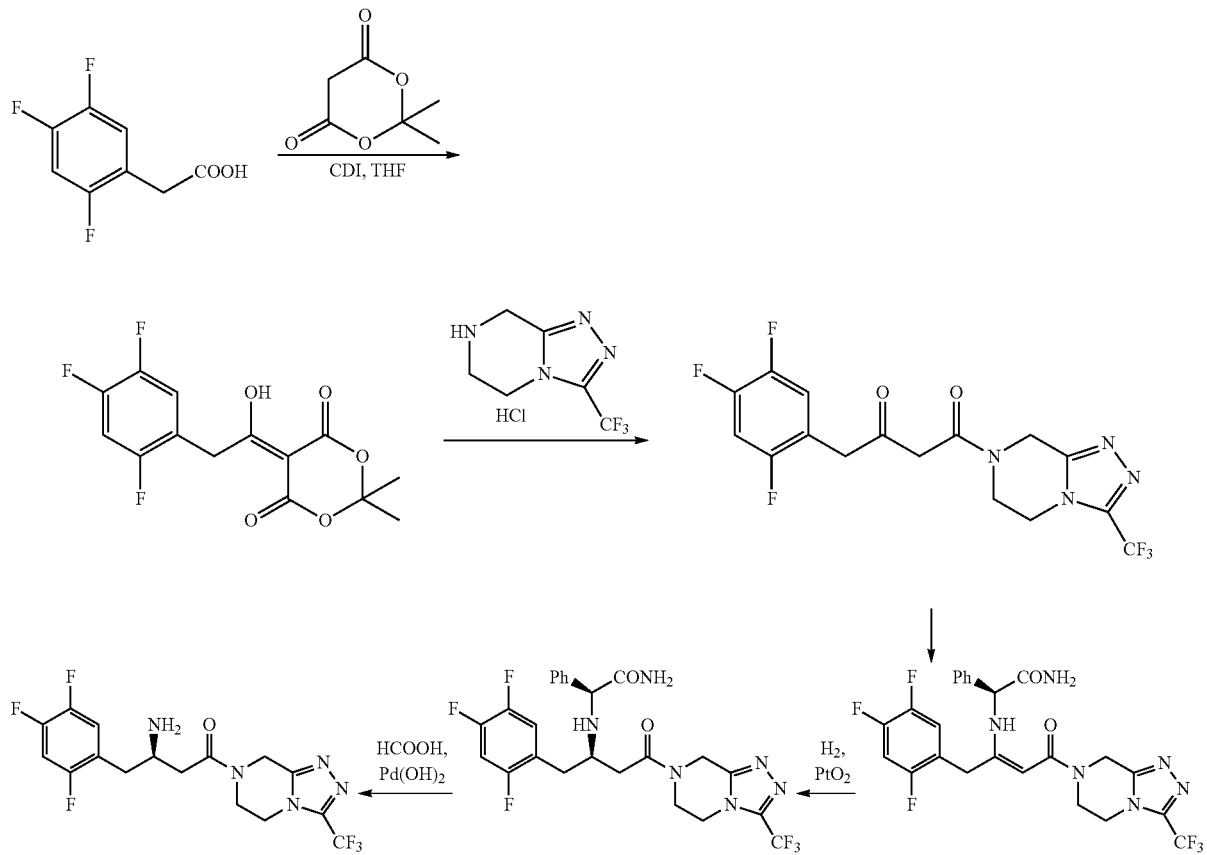
Yet another option is creating chiral centers by selective reduction of β-keto acid derivatives. Precious metal catalysts (WO 04/087650, Org. Prep. Res. & Dev. 9, 634-639 (2005)) or enzymatic reduction (WO 09/045,507) can be used, while the transformation of the obtained chiral hydroxyl intermediates to final sitagliptin precursors via azetidinone intermediates is laborious—Scheme 4.
Scheme 4
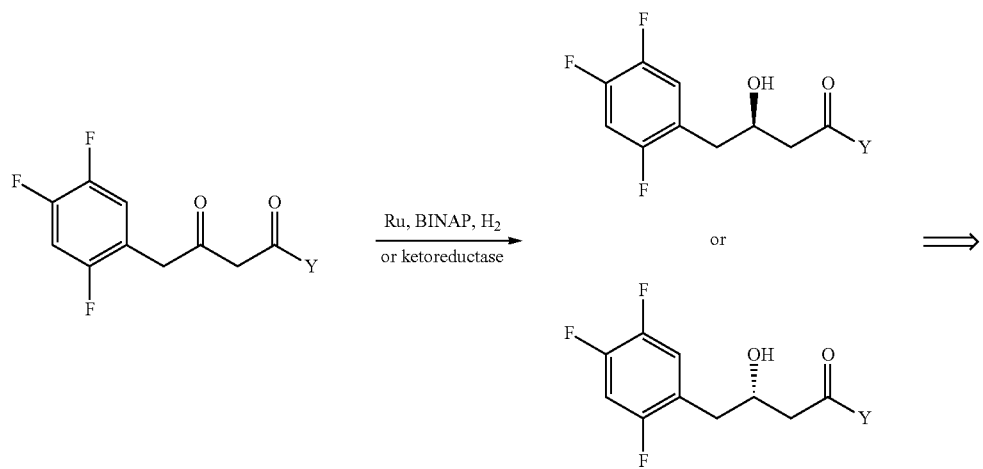

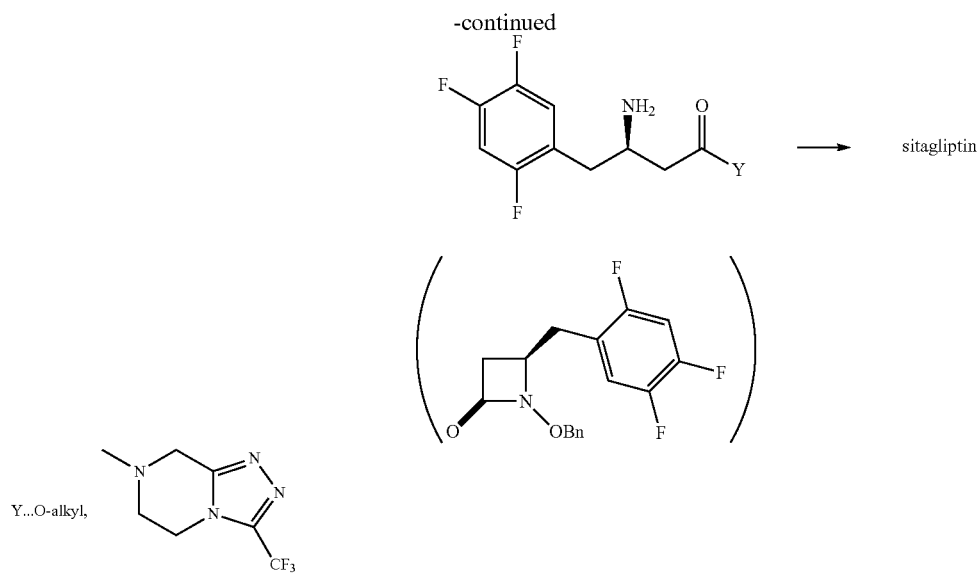

Most of described routes use 2,4,5-trifluorophenylacetic acid derivatives as starting materials which are prepared from 1-bromo-2,4,5-trifluorobenzene via organometal intermediates using copper (US 2004/068141), magnesium (US 2004/077901) and cobalt (CN 1749232) containing reagents. Organometals have been routinely used in industrial synthesis, but it is still more wished to avoid them, because their use requires more expensive special equipment.

Therefore, there is still a need for a simplification of industrial synthesis of β-amino acid derivatives as intermediates in the synthesis of dipeptidyl peptidase-4 (DPP-4) inhibitors such as sitagliptin.

SUMMARY OF THE INVENTION

Aspects, advantageous features and preferred embodiments of the present invention summarized in the following items, respectively alone or in combination, contribute to solving this and other objects of the invention:

1. A process for the preparation of a β-amino amide compound, comprising:
(i) providing a 2-nitropropionic acid derivative of formula (IIc)

wherein Z is
(i-1) a substituent defined by the following formula (III')

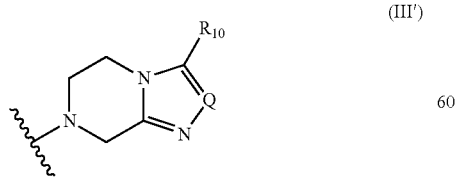

wherein Q is N, CH, C—CF$_3$, or C-phenyl, preferably N, and R$_{10}$ is H, C$_1$-C$_4$-alkyl or fluorinated C$_1$-C$_2$-alkyl, preferably trifluoromethyl, or
(i-2) OH, OR$^1$, NR$^2$R$^3$ or OSiR$^4$R$^5$R$^6$, wherein R$^1$ is C$_1$-C$_6$-alkyl or aryl-C$_1$-C$_2$-alkyl, R$^2$ is H, C$_1$-C$_4$-alkyl, arylmethyl, C$_1$-C$_4$-alkoxy or arylmethoxy, R$^3$ is H, C$_1$-C$_4$-alkyl or arylmethyl and R$^4$, R$^5$ and R$^6$ independently are C$_1$-C$_4$-alkyl or phenyl (ii) carrying out a coupling reaction (condensation) of the 2-nitropropionic acid derivative of formula (IIc) with an aldehyde of formula Ar—CHO, preferably in the presence of a base substance, wherein Ar denotes respectively unsubstituted or substituted phenyl, alkyl-aryl, alkoxy-aryl, and obtaining a compound of formula (VIIIa) or (VIa)

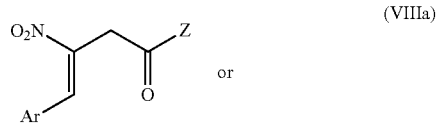

or

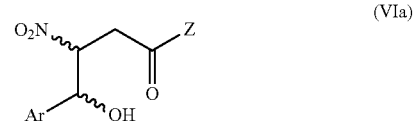

(iii-1) subjecting (VIIIa) or (Via) to a conversion reaction to obtain a compound of (IXa)

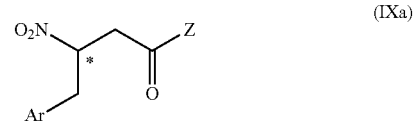

by a reaction selected from the group of esterification, dehydration, reduction, hydrogenation, elimination and combinations thereof, or (iii-2) subjecting (VIIIa) to a reduction reaction to obtain

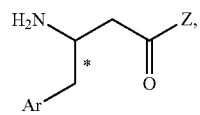 (Ia)

optionally forming a salt thereof;
wherein the stereogenic center marked with an * is either in (R)- or (S)-configuration at marked center, or it is in racemic form,
(iv) if Z is optionally defined as in (i-2), subjecting Z to structural modification, yielding a β-nitro amide compound; and
(v) if the process optionally proceeds via (iii-1) or (iv), reducing the nitro group in compound (Ma) or the reaction products of (iv) to an amino group, optionally forming a salt thereof.

The proceeding with compound (IIc) as defined in (i-1) leads to the advantage that pre-built structural moieties can be provided in high yield in the Z group and can efficiently be coupled with Ar—CHO. The procedural concept of the present invention further allows simple and efficient synthesis schemes starting from readily available or synthesizable starting compounds, as the compound of formula (VIa) provides for useful subsequent synthetic possibilities, and alternatively enables simple conversion to the structural form of formula (VIIIa) with further reaction options. The double bond substituents in formula (VIIIa) can be in a Z- and/or E-configuration, with its individual stereoisomers being separated into either Z- or E-configuration, or forming a Z-/E-mixture, allowing subsequent stereospecific reactions if desired.

Moreover according to the basic procedural concept of the present invention, key structures are obtained which are particularly suitable for inclusion of an β-amino amide framework into more complex molecules. The process according to the present invention allows to obtain a range of β-aminobutyryl compounds, particular those including γ-aryl (especially phenylic) structural moieties in the form of "Ar" defined above, and/or variable structural moieties in the form of "Z" defined above or structurally modified forms, preferably heterocyclic groups. The process according to the present invention is particularly advantageous for producing the characteristic gliptin structure of dipeptidyl peptidase-4 (DPP-4) inhibitors unmet in the above discussed conventional synthetic strategies to obtain gliptins.

In particular, by the process of the present invention synthetic routes are made possible without requiring protective groups and without requiring the use of exotic reagents. Moreover, if desired, stereogenic centers can be efficiently created and eventually resolved into respective stereoisomeric compounds, at least including a putative stereogenic center at the β-carbon atom of the β-amino acid structural framework, thereby enhancing industrial acceptance and suitability of the process of the present invention.

2. The process according to item 1, wherein the step of providing 2-nitropropionic amide derivative of formula (IIc) as defined in (i-1) comprises activating 3-nitropropionic acid of formula (II)

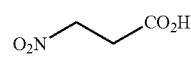 (II)

by conversion to
(i) halogenide of formula (IIa)

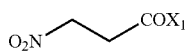 (IIa)

wherein $X_1$ is chloro, bromo, preferably chloro, by reaction with a sulfur, phosphorous, oxalyl or phosgene halogen derivative;
(ii) or anhydride of formula (IIb)

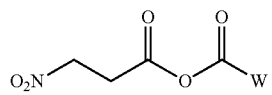 (IIb)

wherein W is selected from the group consisting of $C_1$-$C_6$-alkyl residues, $C_1$-$C_6$-alkoxy residues, unsubstituted or substituted benzyloxy, by reaction with acyl chlorides, preferably pivaloyl chloride, or chloroformates;
(iii) or in situ formed intermediate by reaction with a coupling reagent known from peptide chemistry, selected from the group consisting of
carbodiimides, preferably N,N'-dicyclohexylcarbodiimide (DCC), N,N'-diisopropylcarbodiimide (DPCI), or N-ethyl-N'-(3-dimethyaminopropyl) carbodiimide (EDC), with or without 1-hydroxybenzotriazole;
activated ureas, preferably O-(benzotriazol-1-yl)-N,N,N', N'-tetramethyluronium hexafluorophosphate (HBTU), O-(benzotriazol-1-yl)-N,N,N',N'-tetramethyluronium tetrafluoroborate (TBTU), and O-(7-aza-benzotriazol-1-yl)-N,N,N',N'-tetramethyl uronium hexafluorophosphate (HATU);
carbonyldiimidazole; and
1-methylpyridinium iodide; and
reacting the activated derivative of 3-nitropropanoic acid with the compound (III)

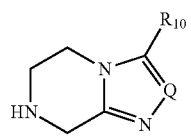 (III)

wherein Q and $R_{10}$ are as defined above.

The activation step is suitably carried out in a solvent, preferably an aprotic solvent, more preferably a solvent selected from halogenated aliphatic hydrocarbons, aromatic hydrocarbons, ethers and nitriles and mixture thereof, preferably acetonitrile.

3. The process according to item 1 or 2, wherein in a preferred embodiment of the present invention the substituent Z as defined under (i-1) has the following formula (IIIa')

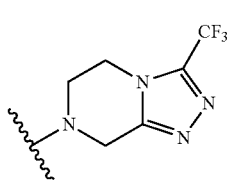
(IIIa')

The preferred embodiment accordingly can beneficially be carried out by reacting an activated 3-nitropropionic acid of formula II according to item 2 with a compound of formula (IIIa) below:

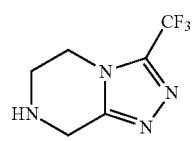
(IIIa)

According to this preferred embodiment, already prepared heterocyclic groups are readily and efficiently coupled to a structural framework from which β-amino amide compounds and valuable intermediate compounds thereof can derive.

The reaction with the compound of formula (IIIa) is suitably carried out in a solvent as described in item 2 above.

4. The process according to any one of the preceding items, wherein the aldehyde Ar—CHO is defined by formula (V)

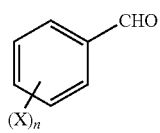
(V)

wherein X is halogen selected from fluoro, chloro, or bromo, preferably fluoro, same or different, and n is 1-4; in a specifically preferred embodiment the aldehyde Ar—CHO is defined by formula (Va)

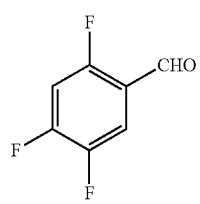
(Va)

This embodiment can beneficially couple aromatic groups to a structural framework from which β-amino amide compounds and valuable intermediate compounds thereof can derive.

The reaction is preferably carried out in the presence of a base substance. Suitable and preferable base substances in the process of the present invention are selected from the group of typically used bases in organic synthesis. The preferred base is selected from inorganic basic salts, such as acetates, carbonates, phosphates, most preferably potassium phosphate tribasic in submolar amounts and possibly even catalytic amounts, preferably in 5-20% molar amount relative to compound (IIc).

The reaction can be suitably carried out in a polar protic or an aprotic solvent, preferably selected from water, alcohols, amides, sulfoxides, sulphones or nitriles, preferably in acetonitrile.

When combined with the specific embodiment of item 1, (i-1), a highly efficient and economic preparation of the compound of formula (VI) can preferably be achieved:

(VI)

Stereogenic centers are marked with an *; these can be either in (R)- or (S)-configuration at marked center, and the reaction typically gives a mixture of stereoisomers. If desired, the stereoisomers can be resolved into the respective (R)- or (S)-isomers. X, n, Q and $R_{10}$ are the same as above.

5. The process according to any one of the preceding items, wherein the compound of formula (VIa) is obtained and subjected to a dehydration reaction by treating said compound with a strong acid or by using a dehydrating agent, respectively to give a compound of formula (VIIIa)

(VIIIa)

wherein Ar and Z are as defined above.

The Ar- and nitro-groups at the double bond can be in a Z- and/or E-configuration, with its individual stereoisomers being separated, or forming a Z-/E-mixture. In a preferred embodiment of the present invention the Ar and the nitro group are in E-configuration.

The strong acid may be selected from, without being limited to, hydrochloric acid, hydrobromic acid, sulfuric acid, methanesulfonic acid, phosphoric acid, polyphosphoric acid. The dehydrating agent may be selected from, without being limited to phosphorus pentoxide, phosphorus oxychloride, molecular sieves, dried aluminium oxide.

When combined with the preferred embodiments of items 1, (i-1) and 4, a highly efficient and economic preparation a compound of formula (VIII) can be achieved according to a further preferred embodiment

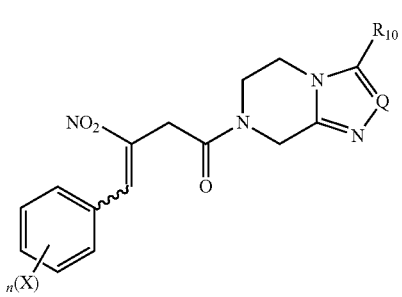
(VIII)

wherein X, n, Q and $R_{10}$ are as defined above.

6. The process according to any one of items 1 to 4, wherein the compound of formula (VIa) is subjected to a reduction reaction to reduce the benzylic hydroxyl group by treatment with silicon hydrides, or by catalytic hydrogenation in the presence of a precious metal catalyst, or by transformation to an ester and catalytic hydrogenation of the ester, respectively to give the compound (IXa)

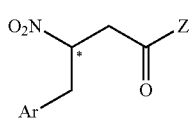
(IXa)

wherein the stereogenic center marked with an * is either in (R)- or (S)-configuration at marked center, or it is in racemic form; and Ar and Z are as defined above.

When combined with the specific embodiments of items 1, (i-1) and 4, a highly efficient and economic preparation a compound of formula (IX) can be achieved according to a further preferred embodiment

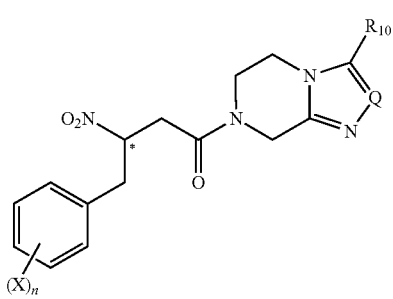
(IX)

Suitable silicon hydrides for the reduction of the benzylic hydroxyl group in (Via) include trialkylsilanes, wherein the alkyl group consists of more than one carbon atom and is preferably ethyl.

7. The process according to any one of the preceding items, wherein the compound of formula (VIa) is subjected to esterification reaction by halogenides or anhydrides of unsubstituted or halogenated $C_1$-$C_6$-alkanoic or $C_1$-$C_6$-alkanesulfonic acids, unsubstituted or para substituted benzenesulfonic acids, respectively in the presence of a base substance to give an ester compound of formula (VIIa)

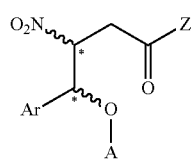
(VIIa)

wherein stereogenic centers are marked with an *; these can be either in (R)- or (S)-configuration at marked center, Ar and Z are as defined above, and A is $C_1$-$C_6$-alkanoyl, halogenated $C_1$-$C_6$-alkanoyl, $C_1$-$C_6$-alkanesulfonyl, unsubstituted or para substituted benzenesulfonyl.

The obtained acylated compound typically is a short-lived intermediate. Beneficially it can be spontaneously converted, suitably under the same or similar reaction conditions of the present esterification step or by way of carrying out a heating step, to a subsequent product eliminating the A-O group as shown in the next item.

When combined with the specific embodiments of items 1, (i-1) and 4, a highly efficient and economic preparation an ester of formula (VII) can be achieved according to a further embodiment

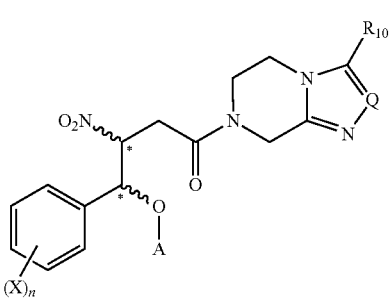
(VII)

wherein stereogenic centers are marked with an *; these can be either in (R)- or (S)-configuration at marked center; and A, X, n, Q and $R_{10}$ are as defined above.

8. The process according to item 7, wherein the ester compound of formula (VIIa) is subjected to base-induced or thermal elimination of AOH from said compound to give a compound of formula (VIIIa)

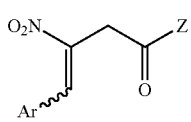
(VIIIa)

The Ar- and nitro-groups at the double bond can be in a Z- and/or E-configuration, with its individual stereoisomers being separated, or forming a Z-/E-mixture.

When combined with the specific embodiments of items 1, (i-1) and 4, preferably a highly efficient and economic preparation a compound of formula (VIII) is achieved

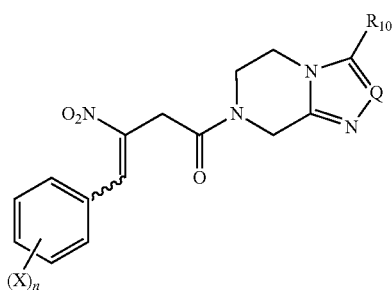

(VIII)

wherein X, n, Q and $R^{10}$ are as defined above.

9. The process according to item 1, 5 or 8, wherein the double bond of formula (VIIIa) is reduced by a reducing agent, by catalytic hydrogenation or by biotransformation, respectively to give a compound of formula (IXa)

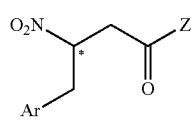

(IXa)

wherein the stereogenic center marked with an * is either in (R)- or (S)-configuration at marked center, or it is in a racemic form, and Ar is as defined above.

Suitable reducing agents include, without being limited to, boron hydrides and aluminium hydrides.

When combined with the specific embodiments of items 1, (i-1) and 4, preferably a highly efficient and economic preparation a compound of formula (IX) is achieved

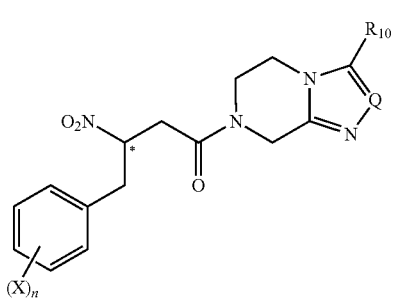

(IX)

wherein the stereogenic center marked with an * is either in (R)- or (S)-configuration at marked center, or it is in racemic form, and X, n, Q and $R_{10}$ are as defined above.

10. The process according to any one of items 1 to 5 and 8, wherein the compound of formula (VIIIa) is subjected to a simultaneous reduction of the double bond and the nitro group by a suitable reduction system to give the compound of formula (Ia)

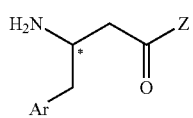

(Ia)

wherein the stereogenic center marked with an * is either in (R)- or (S)-configuration at marked center, or it is in racemic form, Ar and Z are as defined above.

When combined with the preferred specific of items 1, (i-1) and 4, a particularly preferred, efficient and economic preparation of a compound of formula (I) can be achieved

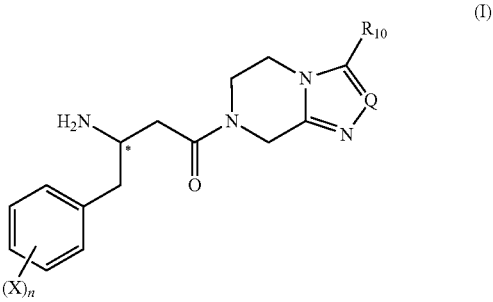

(I)

11. The process according to any one of items 1 to 9, wherein in item 1, (v) the nitro group is converted into an amino group by contacting with a reducing agent, preferably selected from elemental metals in the presence of acids, preferably zinc and tin, cations in low oxidation states selected from Fe(II), Sn(II), Cr(II), hydrogen sulfide, metal sulfides and polysulfides, or by catalytic hydrogenation in the presence of a metal catalyst, preferably selected from nickel, palladium, ruthenium, rhodium, iridium, gold, and platinum, to give the final compound of formula (I).

When combined with the specific embodiment of item 6, preferably the preparation of a compound of formula (I) having included the β-amino amide part coupled to both aromatic and heterocylcle groups is achieved

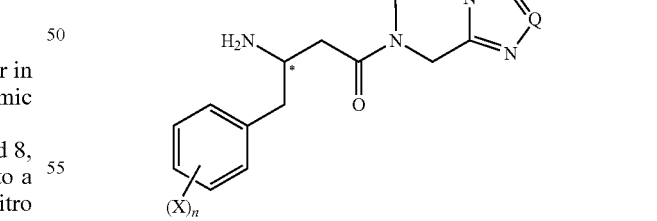

(I)

wherein the stereogenic center marked with an * is either in (R)- or (S)-configuration at marked center, or it is in racemic form, and X, n, Q and $R_{10}$ are as defined above.

The various embodiments of items 1 and 4 to 11 can be summarized by the following scheme (Ar as defined above; Z being defined by (i); stereogenic centers are marked with an *; these can be either in (R)- or (S)-configuration at marked center, or it is in racemic form):

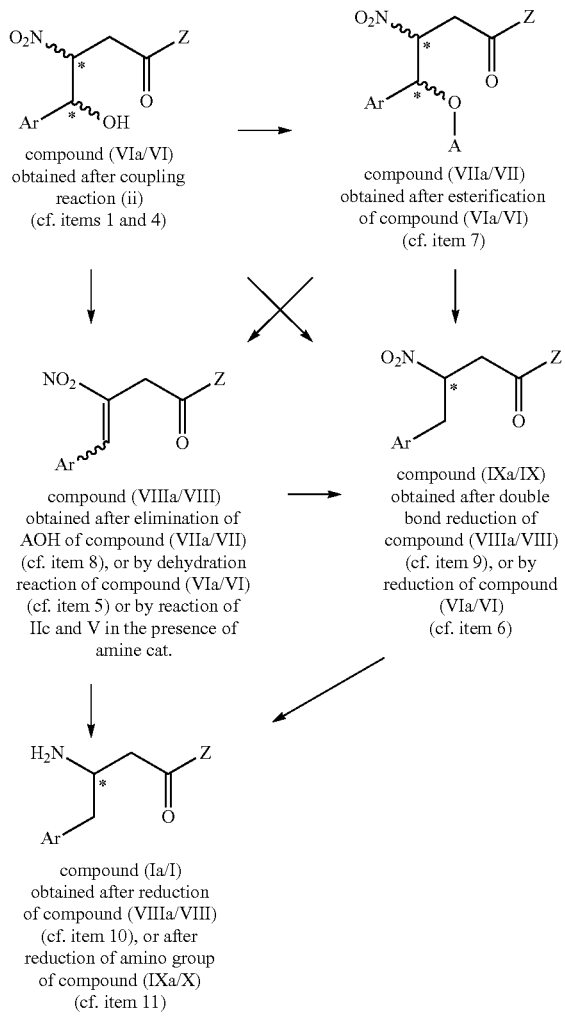

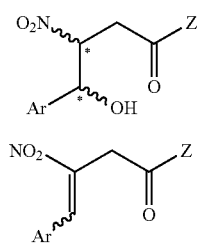

12. The process according to any one of items 1 and 4 to 11, wherein the 2-nitropropionic acid derivative of formula (IIc)

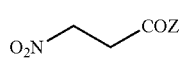

(IIc)

is provided with Z being defined as in item 1, (i-2)

the coupling reaction (ii) with an aldehyde of formula (V) is carried out forming the intermediates (Xa) or (XIIa)

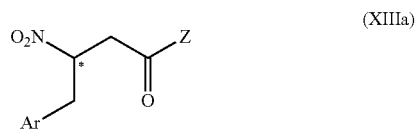

(Xa)

(XIIa)

wherein Ar and * are as defined above, and wherein subsequently the intermediates of formula (Xa), or (XIIa) are subjected to the conversion (iii) to obtain a compound of formula (XIIIa),

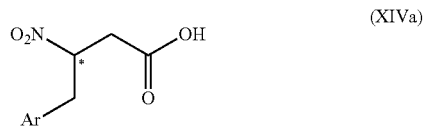

(XIIIa)

wherein compounds of formulae (Xa), (XIIa) and (XIIIa) are respective structural analogues of compounds of formulae (VIa), (VIIIa), and (IXa) in which Z is defined as in item 1, (i-2) and wherein the compound of formula (XIIIa), if Z is other than OH, is converted by a method selected from the group consisting of hydrolysis, reduction and hydrogenation, to give the respective carboxylic compound formula (XIVa)

(XIVa)

which is subjected to further structural modification.

This alternative of proceeding with compound (IIc) with a Z group as defined herein provides the advantage that carboxy, ester or amide groups subsequently can be readily subjected to structural modifications, e.g. as described in item 1, (iv) or (v), to eventually further built-up desirable structural moieties.

Ar is as defined above. More preferably, Ar is

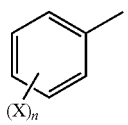

$(X)_n$

Consequently in preferred embodiments of item 12, compounds listed by the following formulae can be effectively obtained in preferred embodiments, respectively (Z being as defined here in item 12):

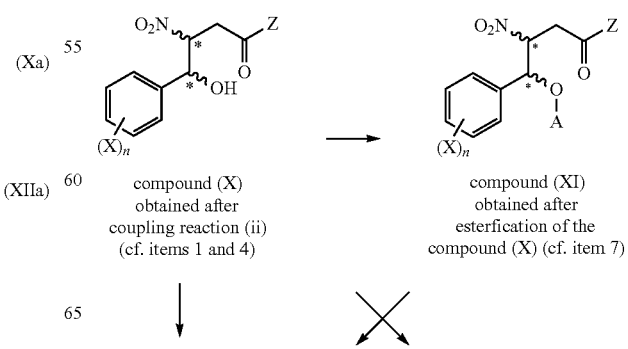

compound (X) obtained after coupling reaction (ii) (cf. items 1 and 4)

compound (XI) obtained after esterfication of the compound (X) (cf. item 7)

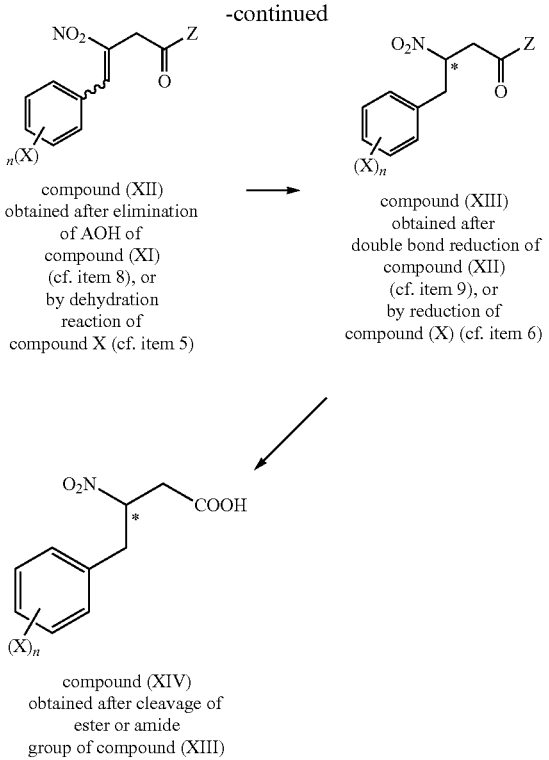

compound (XII)
obtained after elimination
of AOH of
compound (XI)
(cf. item 8), or
by dehydration
reaction of
compound X (cf. item 5)

compound (XIII)
obtained after
double bond reduction of
compound (XII)
(cf. item 9), or
by reduction of
compound (X) (cf. item 6)

compound (XIV)
obtained after cleavage of
ester or amide
group of compound (XIII)

In the compound formulae shown above, stereogenic centers are marked with an *; these can be either in (R)- or (S)-configuration at marked center, or it is in racemic form.

In alternative embodiments, the compound of formula (X) can be dehydrated or the compound of formula (XI) can eliminate AOH, which depending on conditions can occur spontaneously, optionally after additional heating, to obtain the compound of formula (XII) (cf. items 7 and 8). As another alternative, the compound of formula (X) is subjected to dehydration reaction (cf. item 5), to give the compound of formula (XII).

According to another embodiment, the compound of formula (X) is subjected to reduction reaction (cf. item 6), or the compound of formula (XII) is subjected to double bond reduction (cf. item 9), respectively to give the compound of formula (XIII). The compound of formula (XIII) then only needs to be subjected to cleavage reaction of the ester or amide bond present in the Z group.

13. The process according to item 12, wherein subjecting compound of formula (XIV) to further structural modification involves converting the carboxylic group to an activated carboxylic group by (i) reaction with a sulfur, phosphorous, oxalyl or phosgene halogen derivative to obtain respective halogenide $COX_1$, wherein $X_1$ is chloro, bromo, preferably chloro; or (ii) reaction with acyl chlorides, preferably pivaloyl chloride, or chloroformates to obtain an anhydride wherein Z is defined below

wherein W is $C_1$-$C_6$-alkyl or $C_1$-$C_6$-alkoxy, unsubstituted or substituted benzyloxy; or (iii) by reaction with coupling reagents which are ordinary used in peptide chemistry to obtain in situ formed intermediates, wherein the coupling reagents are selected from the group consisting of:
carbodiimides, preferably from N,N'-dicyclohexylcarbodiimide (DCCI), N,N'-diisopropylcarbodiimide (DPCI), or N-ethyl-N'-(3-dimethyaminopropyl) carbodiimide (EDC), with or without 1-hydroxybenztriazole, activated ureas preferably O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), and O-(7-aza-benzotriazol-1-yl)-N,N,N',N'-tetramethyl uronium hexafluorophosphate (HATU)
carbonyldiimidazole,
1-methylpyridinium iodide.

When Ar preferably is

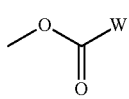

in the preferred embodiments of item 13, compounds listed by the following formulae (XIVa) and (XIVb) can be effectively obtained in preferred embodiments, respectively:

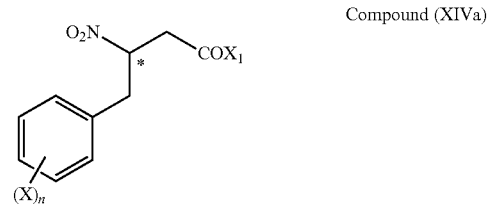

Compound (XIVa)

in accordance with reaction (i) of item 13

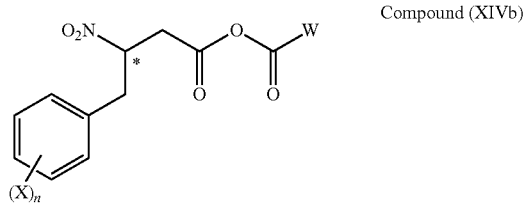

Compound (XIVb)

in accordance with reaction (ii) of item 13 wherein the stereogenic center marked with an * is either in (R)- or (S)-configuration at marked center, or it is in racemic form; and $X_1$ and W is as defined above.

14. The process according to item 13, wherein the activated compound obtained in either one of (i), (ii) or (iii) is reacted with a compound of formula (III)

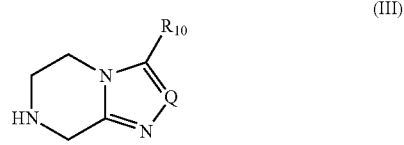

(III)

wherein Q is N, CH, C—$CF_3$, or C-phenyl, preferably N, and $R_{10}$ is H, $C_1$-$C_4$-alkyl or fluorinated $C_1$-$C_2$-alkyl, preferably trifluoromethyl to give a compound of formula (IXb)

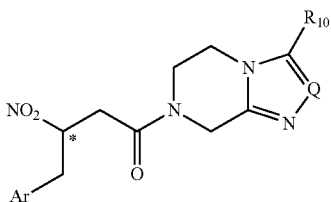

(IXb)

wherein the stereogenic center marked with an * is either in (R)- or (S)-configuration at marked center, or it is in racemic form; and Ar is as defined above;
and subsequently the nitro group is reduced to amino group, preferably as defined in item 11.

When preferably Ar is

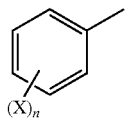

the compound of formula IX can be efficiently obtained

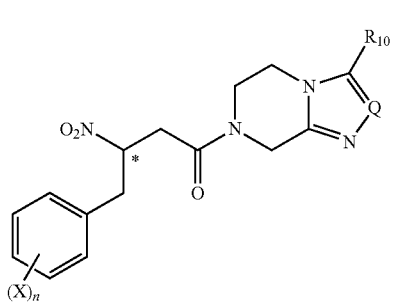

(IX)

wherein the stereogenic center marked with an * is either in (R)- or (S)-configuration at marked center, or it is in racemic form, and X, n, Q and $R_{10}$ are as defined above.

And after reduction of the amino group, the compound of formula (I) can be obtained.

15. The process according to any one of items 1 to 6 and 9 to 14, wherein the β-γ double bond saturation or reduction is respectively carried out in enantioselective manner and enriching either the (R)- or the (S)-enantiomer, preferably the (R)-enantiomer is enriched.

According to this preferred embodiment, the following (R)-enantiomeric stereogenic center is achieved, respectively shown for intermediate nitro compounds as well as for the reduced amino compounds

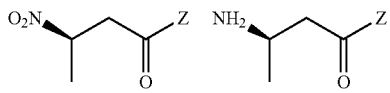

wherein Z and the remaining structure is as defined above.

16. The process according to any one of items 1 to 6 and 9 to 14, wherein the compound of formula (VIIIa/VIII) is subjected to a saturation reaction, preferably a hydrogenation in the presence of a transition metal complexed with at least one auxiliary chiral ligand to give a compound of formula (IXa)

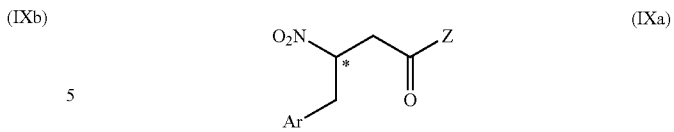

(IXa)

wherein Ar and Z are as defined above,
wherein the configuration on stereogenic center marked with an * is enriched in (R)- or (S)-configuration, preferably is enriched in (R)-enantiomer.

A saturation reaction comprises reactions suitable to saturate a carbon-carbon multiple bond, preferably a double bond, by binding both carbon atoms to hydrogen atoms. Said saturation reaction can take place by a common hydrogenation such as by adding elemental hydrogen to a unsaturated multiple bond or by transfer hydrogenation, wherein the hydrogen is provided by a different source than elemental hydrogen.

When Ar is as preferably defined above the compound of formula (IX) can be efficiently obtained in preferred enantiomeric excess (e.e). values as described below.

The transition metal is preferably selected from nickel, palladium, ruthenium, rhodium, iridium, gold and platinum. The chiral ligand is selected from phosphines, diphosphines, phosphates, phosphites, phosphoroamidites aminoalcohols, diamines, amine-amides, amine-phosphine ligand, or combination thereof such as 2,2'-bis(diphenylphosphino)-1,1'-binaphthyl (BINAP), 1,1-Bis(4-methoxyphenyl)-3-methyl-1, 2-butanediamine (DAIPEN) and 1-(2-diphenylphosphino-1-naphthyl)isoquinoline (QUINAP).

The transition metal and the chiral ligand are preferably provided in the form of readily prepared, preferably homogeneous, catalysts.

Transition metal complexes suitable for being used as catalysts in their own right or in combination with chiral ligands as defined above for saturation reactions such as hydrogenation are selected from the group consisting of bicyclo[2.2.1]hepta-2,5-diene-rhodium(I) chloride dimer, [N-[(1S,2S)-2-(amino-κN)-1,2-diphenylethyl]methanesulfonamidato-κN]chloro[(1,2,3,4,5,6-η)-1,3,5-trimethylbenzene]-ruthenium, chloro[4-methyl-N-[(1R,2R)-2-[(S)-[[2-[(1,2,3,4,5-η)-2,3,4,5-tetramethyl-2,4-cyclopentadien-1-yl]phenyl]methyl]amino-κN]cyclohexyl]benzenesulfonamidato(2-)-κN]-rhodium, dichloro(pentamethylcyclopentadienyl)iridium (III) dimer, dichloro(arene)ruthenium(II) dimer such as dichloro(p-cymene)ruthenium(II) dimer, dichloro(pentamethylcyclopentadienyl)rhodium(III) dimer and bis(1,5-cyclooctadiene)rhodium(I) tetrafluoroborate.

17. The process according to any one of items 1 to 6 and 9 to 12, wherein the compound of formula (VIIIa) is subjected to hydrogenation in the presence of a transition metal complex with at least one achiral ligand to give a compound of formula (IXa)

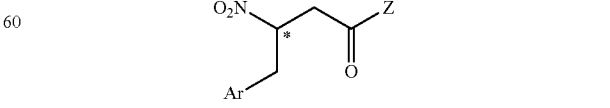

(IXa)

wherein Ar and Z are as defined above,
wherein the configuration on stereogenic center marked with an * is in (R)- or (S)-configuration, where in the product mixture is subjected to a process of enantiomeric separation, preferably by chromatographic means.

18. The process according to any one of items 1 to 6 and 9 to 14, wherein the compound of formula (VIIIa) or (XIIa) is subjected to reduction by a reductase, selected from reductase enzymes of various microorganisms, preferably selected from reductase enzymes derived from *Actinomyces, Saccharomyces* (in particular baker's yeast) or Bacteria genus *Clostridium*.

19. The process according to any one of the preceding items, wherein the amide moiety is defined by the following formula (III)

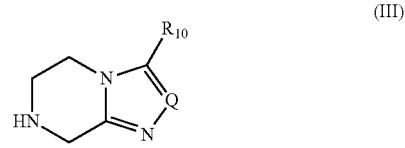

wherein Q is N and $R_{10}$ is trifluoromethyl.

20. The process according to any one of the preceding items, wherein the aldehyde Ar—CHO is defined by formula (Va)

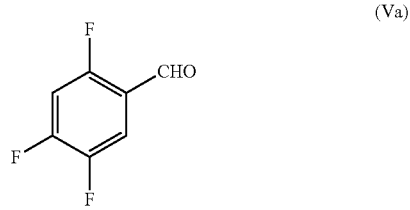

21. A process for an enrichment of one enantiomer of the compound of the formula (IX)

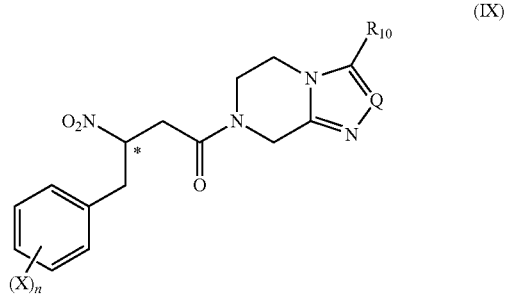

wherein the stereogenic center marked with an * either can be in (R)- or (S)-configuration at marked center; X is halogen selected from fluoro, chloro, or bromo, preferably fluoro, same or different, and n is 1-4, preferably 3, Q is N, CH, C—$CF_3$, or C-phenyl, preferably N, and $R_{10}$ is H, $C_1$-$C_4$-alkyl or fluorinated $C_1$-$C_2$-alkyl, preferably trifluoromethyl, wherein a mixture of both enantiomers is enantiomerically separated by chromatographic means, and a separated desired enantiomer is collected, and wherein a separated undesired enantiomer is subjected to a racemisation reaction to use the racemized mixture of both enantiomers for at least one further enantioselective separation.

22. The process according item 17 or 21, wherein the compound of formula (IX) or (IXa) with the respective stereogenic center * at the β-carbon atom is enriched as the (R)-enantiomer or the (S)-enantiomer, preferably as the (R)-enantiomer.

Enrichment of compound of formula (IX) or (IXa) in one enantiomer can be achieved by enantioselective synthesis and/or by a separation of (R)-enantiomer and (S)-enantiomer using chiral matrix chromatography.

As the method of enantiomer enrichment, any one of the embodiments defined in items 15 to 18 can preferably be used, and/or other conventional ways for enantiomeric enrichment such as chromatographic techniques may be used alternatively or in addition, such as chiral matrix chromatography.

In this manner the (R)-enantiomer or the (S)-enantiomer can be respectively and specifically enriched to over 30% e.e., more preferably to over 60% e.e., most preferably to over 90% e.e.

Most preferable, the compound of formula (IX) or (IXa) is enriched as (R)-enantiomer, preferably to over 60% e.e., more preferably to over 90% e.e., more preferably to over 97%, most preferably to over 99% e.e.

A further advantage of enantiomeric enrichment by chromatographic techniques resides in the effective separation of both enantiomers resulting in highly enriched fractions of the (R)-enantiomer as well as of (S)-enantiomer. Preferably, the retention time of each enantiomer respectively differs from the other significantly, allowing an effective separation.

23. The process according to item 17 or 21, wherein the desired separated enantiomer of the compound of the formula (IX) is the (R)-enantiomer, and the undesired separated enantiomer of the compound of the formula (IX) is the (S)-enantiomer.

An undesired enantiomer e.g. derived by achiral syntheses and/or as side products of enantioselective separation can be re-utilized by racemisation diminishing the unfavorable consequence of a loss of, possibly substantial, amounts of the produced material. Cycles of separation and racemisation allow high yield preparation of one, the desired, enantiomer in a technically suitable and economically desirable manner.

24. The process according to item 21 or 23, wherein the racemisation of the separated undesired enantiomer is carried out in the presence of acid, base or a mixture of acid and base, preferably in the mixture of acid and base, wherein the acid is in molar excess in respect to the base.

25. The process according to item 24, wherein the mixture of acid and base consists of molar excess of acid, preferably consists of 2 to 3 equivalents of acid in respect to base and preferably the amount of base in respect to the compound of formula (IX) is from 0.01 to 100 equivalents, more preferably from 0.5 to 5 equivalents, most preferably from 1 to 3 equivalents.

26. The process according to item 24, wherein the acid is selected from inorganic acid, organic acid or the mixture thereof, preferably from $C_1$-$C_4$ organic acids, preferably the acid is selected from organic acid, more preferably acid is selected from $C_1$-$C_4$ organic acid, most preferably acid is acetic acid.

27. The process according to item 24, wherein the base is selected from inorganic base, organic base or the mixture thereof, preferably from the group of tri-$C_1$-$C_6$-alkylamines, the most preferably the base is triethylamine.

28. The process according to any of items 24 to 27, wherein the reaction is optionally carried out in the presence of a diluting solvent selected from a group of polar solvents, preferably from amides, sulfoxides, nitriles, ketones and alcohols, more preferably from $C_1$-$C_6$ alcohols, most preferably is methanol.

The racemisation is carried out at from 0 to 200° C., preferably reaction is carried out at from 25 to 150° C., most preferably reaction is carried out at from 40 to 100° C. The reaction time is from 1 min to 1 week, preferably from 15 minutes to 24 hours, most preferably from 1 to 8 hours.

29. The process according to any of items 24 to 28, wherein the extent of the racemisation is at least 70%, preferably at least 80%, most preferably at least 90%.

The extent of racemisation refers to the molar ratio of two enantiomers within the range of 1:1 ratio of (S)-enantiomer and (R)-enantiomer (equals 100% racemisation) and only one enantiomer without the other one (equals 0% racemisation).

The preferred embodiments defined in items are industrially acceptable and efficient processes to beneficial prepare DPP-4 inhibitors in high enantiomeric purity.

30. A process for an enrichment of one enantiomer of a chiral compound selected from β-nitrobutyryl amide compounds having a respective stereogenic center at the β-carbon atom, wherein a mixture of both enantiomers of said compound is enantiomerically separated by chromatographic means, and a separated desired enantiomer is collected, and wherein a separated undesired enantiomer is subjected to a racemisation reaction and racemized mixture of both enantiomers is used for at least one further enantioselective separation.

31. The process according to item 30, wherein the compound having the respectively indicated stereogenic center * at the β-carbon atom as set forth in any one of the preceding items is enriched in any of the specified enantiomers.

32. The process according to any one of items 1 to 18 used for the preparation of sitagliptin, wherein the substituents in formulas (I) to (XIII) have the following meaning
  n is 3
  X is fluoro in positions 2, 4 and 5 of benzene ring as regards to the side chain
  Q is N
  $R_{10}$ is trifluoromethyl.

It has thus been demonstrated that the process of the present invention allows to obtain dipeptidyl peptidase-4 (DPP-4) inhibitors in an industrially applicable, economical and acceptable manner.

Preferably, it is readily possible to yield the compound of formula (X) to be in enantiomerically pure form, more preferably is in the (R)-configuration at marked center. Specifically, sitagliptin (compound of formula I) is obtained in a highly efficient process.

33. A compound defined by the following formula (VI)

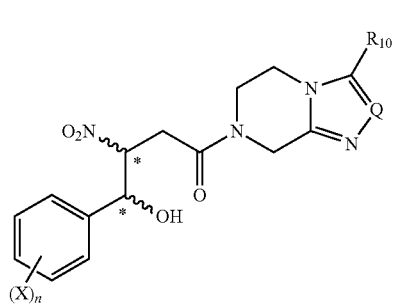

wherein the stereogenic centers marked with an * are either in (R)- or (S)-configuration at marked center; X is halogen selected from fluoro, chloro, or bromo, preferably fluoro, same or different, and n is 1-4, preferably 3; Q is N, CH, C—$CF_3$, or C-phenyl, preferably N; and $R_{10}$ is H, $C_1$-$C_4$-alkyl or fluorinated $C_1$-$C_2$-alkyl, preferably trifluoromethyl.

34. A compound defined by the following formula

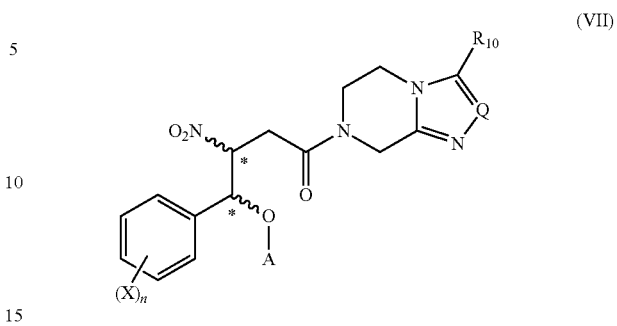

wherein the stereogenic centers marked with an * are either in (R)- or (S)-configuration at marked center; X is halogen selected from fluoro, chloro, or bromo, preferably fluoro, same or different, and n is 1-4, preferably 3; A is $C_1$-$C_6$-alkanoyl, halogenated $C_1$-$C_6$-alkanoyl, $C_1$-$C_6$-alkanesulfonyl, unsubstituted or para substituted benzenesulfonyl; Q is N, CH, C—$CF_3$, or C-phenyl, preferably N; and $R_{10}$ is H, $C_1$-$C_4$-alkyl or fluorinated $C_1$-$C_2$-alkyl, preferably trifluoromethyl.

35. A compound defined by the following formula (VIII)

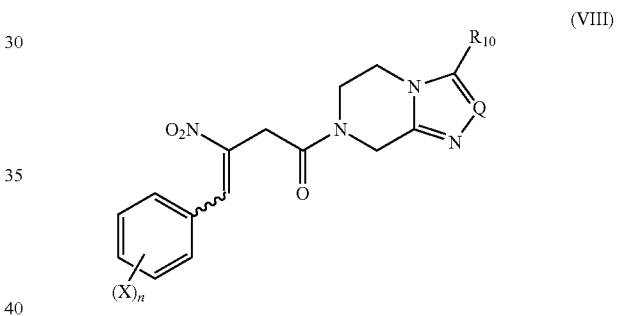

wherein X is halogen selected from fluoro, chloro, or bromo, preferably fluoro, same or different, and n is 1-4, preferably 3; Q is N, CH, C—$CF_3$, or C-phenyl, preferably N; and $R_{10}$ is H, $C_1$-$C_6$-alkyl or fluorinated $C_1$-$C_2$-alkyl, preferably trifluoromethyl.

36. A compound defined by the following formula (IX)

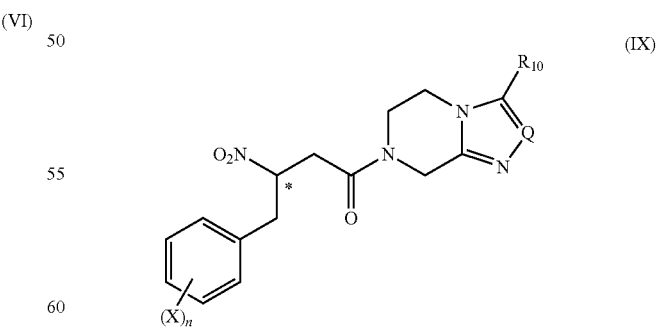

wherein the stereogenic center marked with an * is either in (R)- or (S)-configuration at marked center, or it is in racemic form, preferably in (R)-configuration; X is halogen selected from fluoro, chloro, or bromo, preferably fluoro, same or different, and n is 1-4, preferably 3; Q is N, CH, C—$CF_3$, or C-phenyl, preferably N; and $R_{10}$ is H, $C_1$-$C_4$-alkyl or fluorinated $C_1$-$C_2$-alkyl, preferably trifluoromethyl.

37. 4-Hydroxy-3-nitro-1-(3-(trifluoromethyl)-5,6-dihydro-[1,2,4]triazolo[4,3-a]pyrazin-7(8H)-yl)-4-(2,4,5-trifluorophenyl)butan-1-one of the following formula:

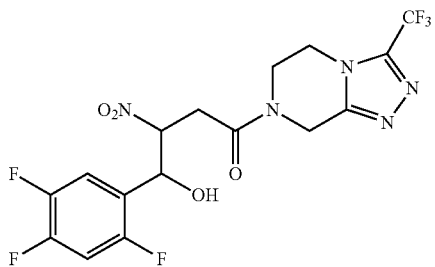 [SMILES: O=C(CC(C(O)c1cc(F)c(F)cc1F)[N+](=O)[O-])N1CCn2c(nnc2C(F)(F)F)C1]

38. 3-Nitro-1-(3-(trifluoromethyl)-5,6-dihydro-[1,2,4]triazolo[4,3-a]pyrazin-7(8H)-yl)-4-(2,4,5-trifluorophenyl)but-3-en-1-one:

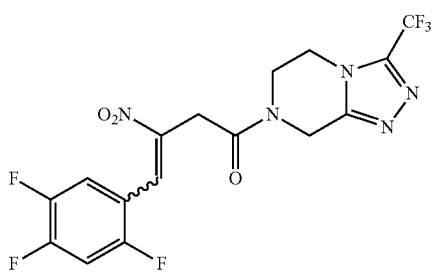 [SMILES: O=C(CC(=Cc1cc(F)c(F)cc1F)[N+](=O)[O-])N1CCn2c(nnc2C(F)(F)F)C1]

39. 3-Nitro-1-(3-(trifluoromethyl)-5,6-dihydro-[1,2,1]-triazolo[4,3-a]pyrazin-7(8H)-yl)-4-(2,4,5-trifluorophenyl)butan-1-one:

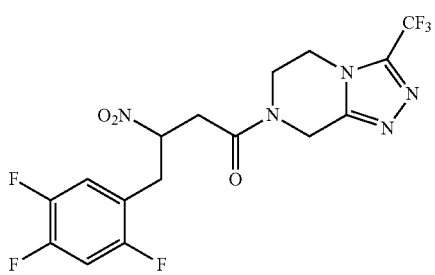 [SMILES: O=C(CC(Cc1cc(F)c(F)cc1F)[N+](=O)[O-])N1CCn2c(nnc2C(F)(F)F)C1]

40. 3-(R)-Nitro-1-(3-(trifluoromethyl)-5,6-dihydro-[1,2,4]triazolo[4,3-a]pyrazin-7(8H)-yl)-4-(2,4,5-trifluorophenyl)butan-1-one:

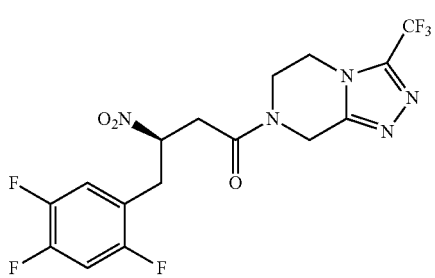 [SMILES: O=C(C[C@@H](Cc1cc(F)c(F)cc1F)[N+](=O)[O-])N1CCn2c(nnc2C(F)(F)F)C1]

The compounds defined in items 36 to 43 respectively specify key intermediates useful for synthesizing gliptins (dipeptidyl peptidase-4 (DPP-4) inhibitors) as particular β-aminobutyryl compounds having γ-phenyl and/or heterocyclic structural moieties. As to preferably enantiomerically enriched compounds, reference is made to item 18 above.

41. Use of a compound as defined in any one of items 36 to 40 for the manufacture of gliptins (dipeptidyl peptidase-4 (DPP-4) inhibitors), preferably sitagliptin.

42. Use of a catalyst comprising a transition metal with at least one chiral ligand, for a saturation reaction of the double bond of the compound of the formula (VIII)

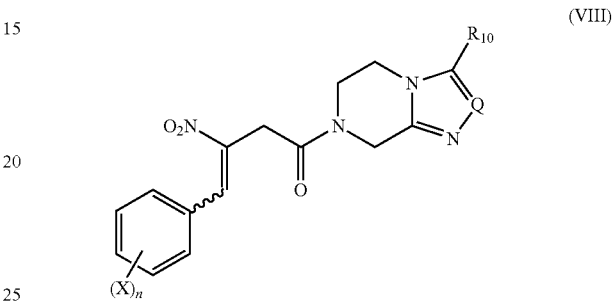

to yield the compound of the formula (IX)

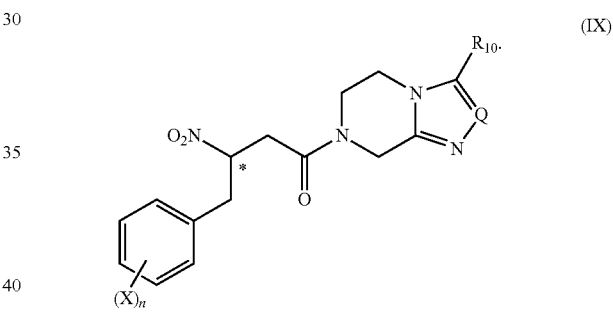

43. Use according to item 42, wherein the transition metal complex is selected from the group of consisting of bicyclo[2.2.1]hepta-2,5-diene-rhodium(I) chloride dimer, [N-[(1S,2S)-2-(amino-κN)-1,2-diphenylethyl]methanesulfonamidato-κN]chloro[(1,2,3,4,5,6-η)-1,3,5-trimethylbenzene]-ruthenium and chloro[4-methyl-N-[(1R,2R)-2-[(S)-[[2-[(1,2,3,4,5-η)-2,3,4,5-tetramethyl-2,4-cyclopentadien-1-yl]phenyl]methyl]amino-κN]cyclohexyl]benzenesulfonamidato(2-)-κN]-rhodium; or wherein the transition metal complex is prepared from a transition metal complex precursor selected from the group consisting of dichloro(pentamethylcyclopentadienyl)iridium (III) dimer, dichloro(arene)ruthenium(II) dimer such as dichloro(p-cymene)ruthenium(II) dimer, dichloro(pentamethylcyclopentadienyl)rhodium(III) dimer and bis(1,5-cyclooctadiene)rhodium(I) tetrafluoroborate, and a chiral ligand selected from the group consisting of phosphines, diphosphines, phosphates, phosphites, phosphoroamidites aminoalcohols, diamines, amine-amides, amine-sulfonamide, amine-phosphine ligand, or combination thereof.

44. Use according to item 42 or 43, wherein the chiral ligand is 2,2'-bis(diphenylphosphino)-1,1'-binaphthyl (BINAP).

45. Process for the preparation of a pharmaceutical composition comprising a gliptin (dipeptidyl peptidase-4 (DPP-4) inhibitor), comprising:

carrying out a process according to any one of items 1 to 29 and obtaining a gliptin compound;
optionally transforming said gliptin compound into its pharmaceutically acceptable salt
formulating said gliptin compound or its pharmaceutically acceptable salt with at least one pharmaceutical excipient.

46. The process according to item 45, wherein said gliptin is sitagliptin.

47. The process according to item 45, wherein said gliptin compound, preferably sitagliptin, is transformed into its phosphate salt.

48. The process according to any one of items 48 to 50, wherein said pharmaceutical composition comprises a combination of said gliptin compound and one or more additional pharmaceutically active ingredient(s), preferably selected from the group consisting of insulin sensitizers, insulin, insulin mimetics, sulfonylureas, α-glucosidase inhibitors, glucagon receptor antagonists, GLP-1, GLP-1 analogues, GLP-1 mimetics, GLP-1 receptor agonists, GIP, GIP mimetics, PACAP, PACAP mimetics, PACAP receptor agonists, cholesterol lowering agents, PPARδ agonists, antiobesity compounds, ileal bile acid tranporter inhibitors, agents intended for use in inflammatory conditions, antihypertensive agents, glucokinase activators (GKAs), inhibitors of 11β-hydroxysteroid dehydrogenase type 1, inhibitors of cholesteryl ester transfer protein (CETP) and inhibitors of fructose 1,6-bisphosphatase.

49. The process according to item 51, wherein said additional pharmaceutically active ingredient is metformin or its pharmaceutically acceptable salt.

DETAILED DESCRIPTION OF THE INVENTION

The present invention provides an industrially applicable, economical and acceptable preparation of β-aminobutyryl substituted compounds, in particular β-aminobutyryl compounds having γ-phenyl and/or heterocyclic structural moieties, which thereby leads to useful key structure framework of modern drug chemistry and especially of antidiabetic agents dipeptidyl peptidase-4 (DPP-4) inhibitors such as sitagliptin. The preparation process start from 3-nitroproprionic acid or derivatives thereof, and can preferably use 2,4,5-trifluorobenzaldehyde in the advantageous embodiment to prepare gliptin and related structures, as respective cheap commercial starting materials. 2,4,5-trifluorobenzaldehyde as the further starting compound for the preparation of gliptins is a product of classical fluoro chemistry without the need for organometals for its preparation. β-nitro propionic acid and its substituted forms and derivatives are easily available from corresponding acrylic derivatives. Moreover, the process of the present invention provides excellent options to introduce chiral centers at the β-carbon atom of the β-amino acid derivatives.

α-Hydroxy-β-amino butyric acid derivatives can be prepared by a condensation reaction of an α-hydroxy-β-nitro propionic acid and an aldehyde and subsequent reduction of the nitro group using Pd/C or Pd, respectively as hydrogenation catalyst. (JP7165678 (A), Chin. J. Med. Chem., 13, 5, 270). However, α-hydroxy-β-nitro propionic acid are no suitable precursors for the synthesis of gliptins and in particular of sitagliptin.

The term "alkyl" as used herein, if not stated otherwise with respect to particular embodiments, includes reference to a straight or branched chain alkyl moiety having 1, 2, 3, 4, 5 or 6 carbon atoms. This term includes methyl, ethyl, propyl (n-propyl or isopropyl), butyl (n-butyl, sec-butyl or tert-butyl), pentyl, hexyl and the like. In particular, alkyl may have 1, 2, 3 or 4 carbon atoms.

The term "cycloalkyl" as used herein, if not stated otherwise with respect to particular embodiments, includes an alicyclic moiety having 3, 4, 5, 6, 7 or 8 carbon atoms. The group may be a bridged or polycyclic ring system. More often cycloalkyl groups are monocytic. This term includes groups such as cyclopropyl, cyclobutyl, cyclopentyl, cyclohexyl, norbornyl, bicyclo[2.2.2]octyl and the like.

The term "alkoxy" as used herein, if not stated otherwise with respect to particular embodiments, include —O-alkyl, wherein alkyl is straight or branched chain and comprises 1, 2, 3, 4, 5 or 6 carbon atoms. In certain embodiments, alkoxy has 1, 2, 3 or 4 carbon atoms. This term includes methoxy, ethoxy, propoxy, isopropoxy, butoxy, tert-butoxy, pentoxy, hexoxy and the like.

The term "aryl" as used herein, if not stated otherwise with respect to particular embodiments, includes reference to an aromatic ring system comprising 6, 7, 8, 9, 10, 11, 12, 13, 14, 15 or 16 ring carbon atoms. Aryl is often phenyl but may be a polycyclic ring system, having two or more rings, at least one of which is aromatic.

This term includes phenyl, naphthyl, fluorenyl, azulenyl, indenyl, anthryl and the like.

The term "arene" as used herein, if not stated otherwise with respect to particular embodiments, includes reference to an aromatic ring system comprising 6, 7, 8, 9, 10, 11, 12, 13, 14, 15 or 16 ring carbon atoms. Arene is often benzene but may be a polycyclic ring system, having two or more rings, at least one of which is aromatic.

This term includes benzene, p-cymene, mesitylene, anisol, hexamethylbenzene and the like.

The term "heterocycle" as used herein includes, if not stated otherwise with respect to particular embodiments, a saturated (e.g. heterocycloalkyl) or unsaturated (e.g. heteroaryl) heterocyclic ring moiety having 3, 4, 5, 6, 7, 8, 9, 10, 11, 12, 13, 14, 15 or 16 ring atoms, at least one of which is selected from nitrogen and oxygen. In particular, heterocyclyl includes a 3- to 10-membered ring or ring system and more particularly a 5- or 6- or 7-membered ring, which may be saturated or unsaturated; examples thereof include oxiranyl, azirinyl, 1,2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, β-carbolinyl, phenanthridinyl, acridinyl, perimidinyl, phenanthrolinyl, furazanyl, phenazinyl, phenothiazinyl, phenoxazinyl, ehromenyl, isochromanyl, chromanyl and the like.

More specifically, a saturated heterocyclic moiety may have 3, 4, 5, 6 or 7 ring carbon atoms and 1, 2, 3, 4 or 5 ring heteroatoms selected from nitrogen and oxygen. The group may be a polycyclic ring system but more often is monocytic, for example including azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolinidinyl and the like. Furthermore, the "heteroaryl" may include an aromatic heterocyclic ring system having 5, 6, 7, 8, 9, 10, 11, 12, 13, 14, 15 or 16 ring atoms, at least one of which is selected from nitrogen and oxygen. The group may be a polycyclic ring system, having two or more rings, at least one of which is aromatic, but is more often monocyclic. This term includes pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, purinyl, isoquinolinyl, quinazolinyl, pteridinyl and the like.

The term "substituted" as used herein in reference to a structure/moiety/group means that one or more, especially up to 5, more especially 1, 2 or 3, of the hydrogen atoms in said structure/moiety/group are replaced independently of each other by the corresponding number of substituents known to a person skilled in the art. Typical substituents include, without being limited to halogen, trifluoromethyl, cyano, nitro, oxo, NR', —OR', —C(O)R', —C(O)OR', —OC(O)R', —S(O)R', N(R)R", C(O)N(R')R'", —SO$_2$N(R')R'" and wherein each of R', R" and R'" are selected from the group consisting of $C_1$-$C_6$ alkyl, $C_1$-$C_6$ alkoxy, —(CH$_2$)$_m$-heterocyclyl (m being 1, 2, 4 or 4) and each R' and R" may be optionally and independently further substituted with one or more of hydrogen, halogen, cyano, amino, hydroxy, $C_1$-$C_6$ alkyl and $C_1$-$C_6$ alkoxy. Specific substituents in particular include halogen such as fluoro, chloro and/or bromo, hydroxy, amino, $C_1$-$C_6$ alkyl and $C_1$-$C_6$ alkoxy, and halogenated $C_1$-$C_6$ alkyl and $C_1$-$C_6$ alkoxy such as trifluoro-methyl. It will be understood that substituents are at positions where they are chemically possible, it being known or evident to the person skilled in the art to decide (either experimentally or theoretically) without inappropriate effort whether a particular substitution is possible. For example, substituents which may be unstable or may affect reactions disclosed herein may be omitted, at least at the relevant stage of intermediate compound or of the affected reaction.

The term "base substance" used herein according to preferred embodiments can be any base known and typically used in organic synthesis. The base can include, without being limited to, amides, hydrides, hydroxides, amidines, tertiary amines. The preferred base is selected from inorganic basic salts, such as acetates, carbonates, phosphates, most preferably potassium phosphate tribasic in submolar amounts and possibly even catalytic amounts, preferably in 5-20% molar amount relative to compound (IIc).

According to a preferred option (A) of an embodiment of the present invention for the synthesis of dipeptidyl peptidase-4 (DPP-4) inhibitors of formula (I)

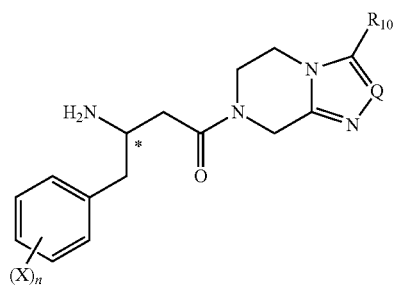

wherein the stereogenic center marked with an * is either in (R)- or (S)-configuration at marked center, or it is in racemic form, X is halogen selected from fluoro, chloro or bromo, preferably fluoro, same or different, n is 1-4, Q is N, CH, C—CF$_3$, or C-phenyl, preferably N, and $R_{10}$ is H, $C_1$-$C_4$-alkyl or fluorinated $C_1$-$C_2$-alkyl, preferably trifluoromethyl comprises (a) activating 3-nitropropionic acid of formula (II)

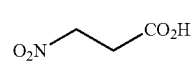

by conversion to
(i) halogenide of formula (IIa)

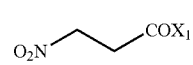

wherein $X_1$ is chloro, bromo, preferably chloro, by reaction with a sulfur, phosphorous, oxalyl or phosgene halogen derivative,
(ii) anhydride of formula (IIb)

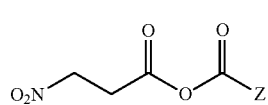

wherein Z is $C_1$-$C_8$-alkyl or $C_1$-$C_6$-alkoxy, unsubstituted or substituted benzyloxy with acyl chlorides, preferably pivaloyl chloride, or chlorofomate,
(iii) in situ formed intermediates by coupling reagents which are ordinary used in peptide chemistry, selected from
carbodiimides, preferably from N,N'-dicyclohexylcarbodiimide (DCC), N,N'-diisopropylcarbodiimide (DPCI), or N-ethyl-N'-(3-dimethyaminopropyl) carbodiimide (EDC), with or without 1-hydroxybenzotriazole,
activated ureas preferably O-(benzotriazol-1-yl)-N,N,N',N'-tetramethyluronium hexafluorophosphate (HBTU), O-(benzotriazol-1-yl)-N,N,N',N'-tetramethyl uronium tetrafluoroborate (TBTU), and O-(7-aza-benzotriazol-1-yl)-N,N,N',N'-tetramethyl uronium hexafluorophosphate (HATU)
carbonyldiimidazole,
1-methylpyridinium iodide.
(b) reaction of the activated derivative of 3-nitropropanoic acid with a compound of formula (III)

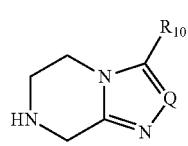

Q is N, CH, C—CF$_3$, or C-phenyl, preferably N, and $R_{10}$ is H, $C_1$-$C_4$-alkyl or fluorinated $C_1$-$C_2$-alkyl, preferably trifluoromethyl to give a compound of formula (IV)

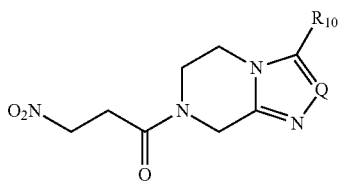

(IV)

wherein Q and R$_{10}$ are as described above (c) condensation of the compound of formula (IV) with an aromatic aldehyde of formula (V)

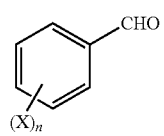

(V)

wherein X is halogen selected from fluoro, chloro, or bromo, preferably fluoro, same or different, and n is 1-4, in the presence of bases to give a mixture of compounds of formula (VI)

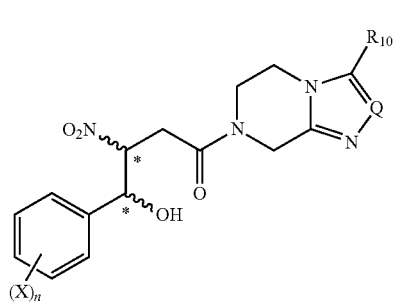

(VI)

wherein the stereogenic centers marked with an * are either in (R)- or (S)-configuration at marked center, and X, n, Q and R$_{10}$ are the same as above (d) esterification of the compound of formula (VI) by halogenides or anhydrides of unsubstituted or halogenated C$_1$-C$_6$-alkanoic or C$_1$-C$_6$-alkanesulfonic acids, unsubstituted or para substituted benzenesulfonic acids in the presence of bases to give an ester of formula (VII)

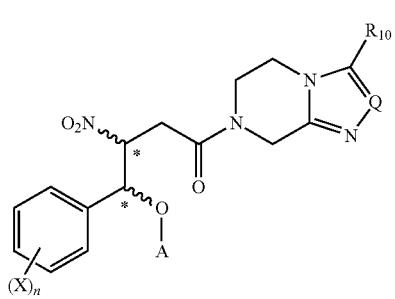

(VII)

wherein A is C$_1$-C$_6$-alkanoyl, halogenated C$_1$-C$_6$-alkanoyl, C$_1$-C$_6$-alkanesulfonyl, unsubstituted or para substituted benzenesulfonyl, and X, n, Q and R$_{10}$ are the same as above, which normally is a short-live intermediate and can spontaneously be submitted to conversion of step (e) in reaction conditions of step (d)

(e) spontaneous, base induced or thermal, elimination of AOH from the compound of formula (VII) to give a compound of formula (VIII)

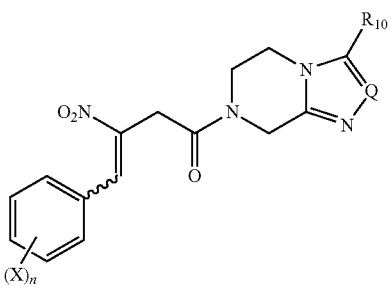

(VIII)

wherein X, n, Q and R$_{10}$ are the same as above, (f) saturation of the double bond by reducing agents, such as boron or aluminium hydrides, by catalytic hydrogenation or biotransformation to give a compound of formula (IX)

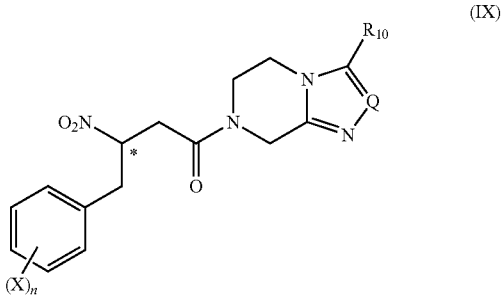

(IX)

wherein the stereogenic center marked with an * is either in (R)- or (S)-configuration at marked center, or it is in racemic form, and X, n, Q and R$_{10}$ are the same as above, optionally performing an enantimeric enrichment by chromatographic techniques, (g) reduction of nitro group by reducing agents preferably selected from elemental metals in the presence of acids, preferably zinc and tin, cations in low oxidation states selected from Fe(II), Sn(II), Cr(II), hydrogen sulfide, metal sulfides and polysulfides, or by catalytic hydrogenation in the presence of nickel, palladium, platinum catalysts to give the final compound of formula (I).

According to another option (B) of the embodiment present invention for the synthesis of dipeptidyl peptidase-4 (DPP-4) inhibitors, the compound of formula (VI) of the step (c) is dehydrated spontaneously in the conditions of the step (c) or after additional heating to give the compound of formula (VIII), so steps (d) and (e) are not necessary and are subsequently omitted.

In another optional embodiment (C) steps (d) and (e) of the option (A) are replaced by
(h) dehydration reaction in which compound of formula (VI)

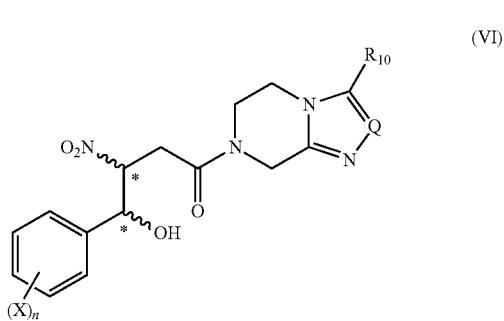

(VI)

wherein the stereogenic centers marked with an * are either in (R)- or (S)-configuration at marked center, and X, n, Q and $R_{10}$ are the same as above
is treated with a strong acid such as hydrochloric acid, hydrobromic acid, sulfuric acid, methanesulfonic acid, phosphoric acid, polyphosphoric acid or by using a dehydrating agent selected but not limited to phosphorus pentoxide, phosphorus oxychloride, molecular sieves, dried aluminium oxide to give the compound of formula (VIII)

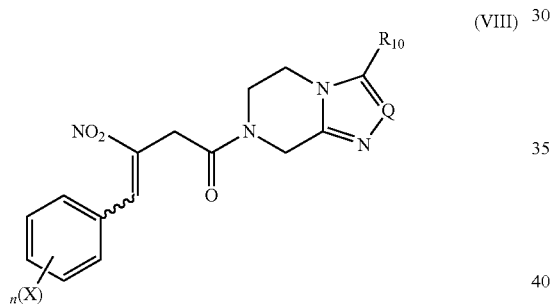

(VIII)

wherein and X, n, Q and $R_{10}$ are the same as above.

In another optional embodiment (D) steps (d), (e) and (f) of the option (A) are replaced by
(i) reduction of the benzylic hydroxy group of compound of formula (VI)

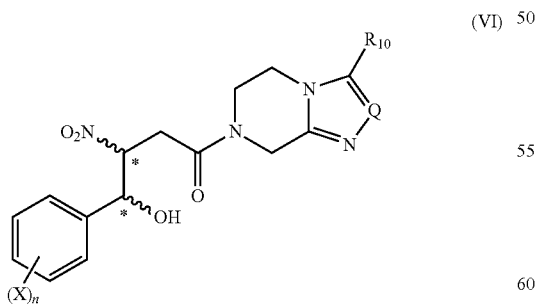

(VI)

wherein the stereogenic centers marked with an * are either in (R)- or (S)-configuration at marked center, and X, n, Q and $R_{10}$ are the same as above,
by treating with silicon hydrides such as triethylsilane, or by catalytic hydrogenation on precious metal catalyst, or by transformation of the compound (VI) to ester (VII) according to step (d) and catalytic hydrogenation of the ester to give the compound (IX)

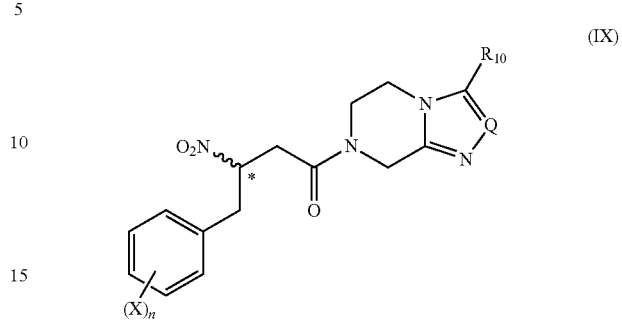

(IX)

wherein the stereogenic center marked with an * is either in (R)- or (S)-configuration at marked center, or it is in racemic form, and X, n, Q and $R_{10}$ are the same as above,
optionally performing an enantiomeric enrichment by chromatographic techniques.

In another optional embodiment (E) steps (f) and (g) of the option (A) are replaced by
(j) simultaneous reduction of double bond and nitro group in which the compound of formula (VIII)

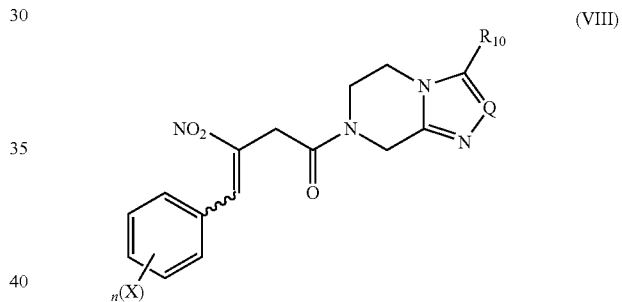

(VIII)

wherein and X, n, Q and $R_{10}$ are the same as above,
is treated with a reducing agent, such as lithium aluminium hydride, sodium borohydride or boron trifluoride or by hydrogenation on metal catalysts to give the compound of formula (I)

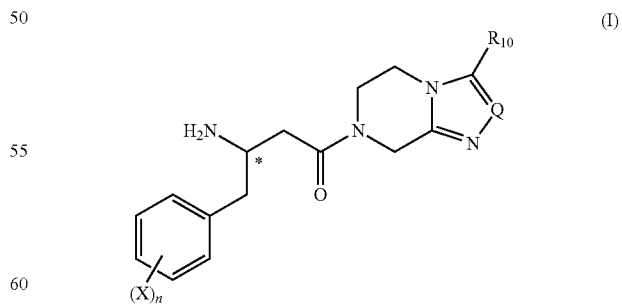

(I)

wherein the stereogenic center marked with an * is either in (R)- or (S)-configuration at marked center, X, n, Q and $R_{10}$ are the same as above.

In another optional embodiment (F) steps (a)-(f) of the option (A) are replaced by the following set of steps (k) condensation of the nitropropionic derivative of formula (IIc)

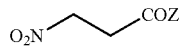
(IIc)

wherein Z is $OH$, $OR^1$, $NR^2R^3$ or $OSiR^4R^5R^6$, wherein $R^1$ is $C_1$-$C_8$-alkyl or aryl-$C_1$-$C_2$-alkyl, $R^2$ is H, $C_1$-$C_4$-alkyl, arylmethyl, $C_1$-$C_4$-alkoxy or arylmethoxy, $R^3$ is H, $C_1$-$C_4$-alkyl or arylmethyl and $R^4$, $R^5$ and $R^6$ independently are $C_1$-$C_4$-alkyl or phenyl with the aldehyde of formula (V)

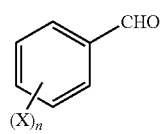
(V)

wherein X is halogen selected from fluoro, chloro, or bromo, preferably fluoro, same or different, and n is 1-4, in the presence of bases to give a mixture of compounds of formula (X)

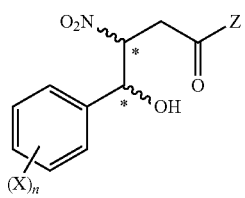
(X)

wherein the stereogenic centers marked with an * are either in (R)- or (S)-configuration at marked center, and X, n and Z are the same as above, (l) esterification of the compound of formula (X) by halogenides or anhydrides of unsubstituted or halogenated $C_1$-$C_6$-alkanoic or $C_1$-$C_8$-alkanesulfonic acids, unsubstituted or para substituted benzenesulfonic acids in the presence of bases to give an ester of formula (XI)

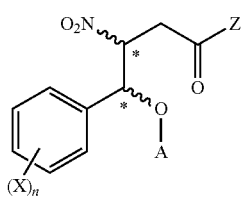
(XI)

wherein A is $C_1$-$C_6$-alkanoyl, halogenated $C_1$-$C_6$-alkanoyl, $C_1$-$C_6$-alkanesulfonyl, unsubstituted or para substituted benzenesulfonyl, and A, X, n and Z are the same as above, which is in most cases a short-live intermediate, spontaneously submitted to conversion of step (m) in reaction conditions of step (l)

(m) spontaneous, base induced, or thermal elimination of AOH to give a compound of formula (XII)

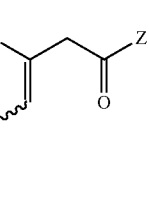
(XII)

wherein and X, n and Z are the same as above, (n) saturation of the double bond by reducing agents, such as boron or aluminium hydrides, by catalytic hydrogenation or biotransformation to give a compound of formula (XIII)

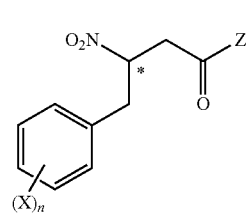
(XIII)

wherein the stereogenic center marked with an * is either in (R)- or (S)-configuration at marked center, or it is in racemic form, and X, n and Z are the same as above, (o) if Z is other than OH cleavage of the ester or amide group of the compound of formula (XIII), wherein Z is $OR^1$, $NR^2R^3$ or $OSiR^4R^5R^6$, wherein $R^1$ is $C_1$-$C_6$-alkyl or aryl-$C_1$-$C_2$-alkyl, $R^2$ is H, $C_1$-$C_4$-alkyl, arylmethyl, $C_1$-$C_4$-alkoxy or arylmethoxy, $R^3$ is H, $C_1$-$C_4$-alkyl or arylmethyl and $R^4$, $R^5$ and $R^6$ independently are $C_1$-$C_4$-alkyl or phenyl by conventional methods of hydrolysis, reduction or hydrogenation to give the compound of formula (XIV)

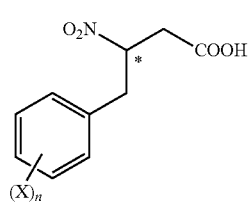
(XIV)

wherein X and n are the same as above (p) conversion the compound of formula (XIV) to
   (i) halogenide of formula (XIVa)

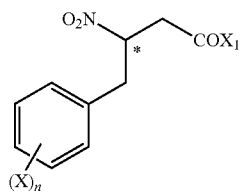
(XIVa)

wherein $X_1$ is chloro, bromo, preferably chloro, by reaction with a sulfur, phosphorous, oxalyl or phosgene halogen derivative, (ii) anhydride of formula (XIVb)

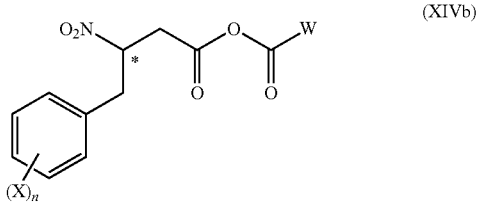

wherein W is $C_1$-$C_6$-alkyl or $C_1$-$C_6$-alkoxy, unsubstituted or substituted benzyloxy with acyl chlorides, preferably pivaloyl chloride, or chloroformates, (iii) in situ formed intermediates by coupling reagents which are ordinary used in peptide chemistry, selected from carbodiimides, preferably from N,N'-dicyclohexylcarbodiimide (DCC), N,N'-diisopropylcarbodiimide (DPCI), or N-ethyl-N'-(3-dimethyaminopropyl) carbodiimide (EDC), with or without 1-hydroxybenztriazole, activated ureas preferably O-(benzotriazol-1-yl)-N,N,N', N'-tetramethyluronium hexafluorophosphate (HBTU), O-(benzotriazol-1-yl)-N,N,N',N'-tetramethyluronium tetrafluoroborate (TBTU), and O-(7-aza-benzotriazol-1-yl)-N,N,N',N'-tetramethyluronium hexafluorophosphate (HATU)

carbonyldiimidazole, 1-methylpyridinium iodide.

(q) reaction of the activated derivative of the acid of formula (XIV) with a compound of formula (V)

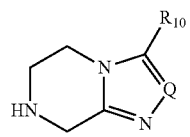

Q is N, CH, C—$CF_3$, or C-phenyl, preferably N, and $R^{10}$ is H, $C_1$-$C_4$-alkyl or fluorinated $C_1$-$C_2$-alkyl, preferably trifluoromethyl to give a compound of formula (IX)

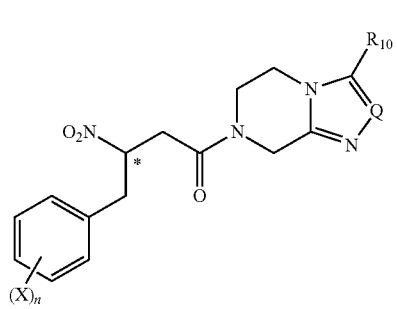

wherein the stereogenic center marked with an * is either in (R)- or (S)-configuration at marked center, or it is in racemic form, and X, n, Q and $R_{10}$ are the same as above, and the obtained compound is further treated according to the step (g) of the option (A).

In the option (G) of the present invention the compound of formula (X) of the step (k) of option (F) is dehydrated spontaneously in the conditions of the step (k) or after additional heating to give the compound of formula (XII), so steps (l) and (m) are not necessary and are subsequently omitted.

In another optional embodiment (H) steps (l) and (m) of the option (F) are replaced by (r) dehydration reaction in which compound of formula (X)

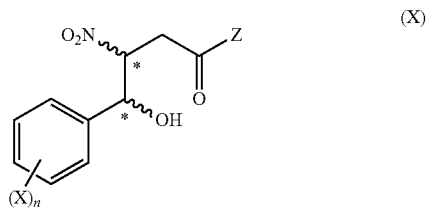

wherein the stereogenic centers marked with an * are either in (R)- or (S)-configuration at marked center, and X, n and Z are the same as above, is treated with strong acid such as hydrochloric acid, hydrobromic acid, sulfuric acid, methanesulfonic acid, phosphoric acid, polyphosphoric acid or by using a dehydrating agent selected but not limited to phosphorus pentoxide, phosphorus oxychloride, molecular sieves, dried aluminium oxide to give the compound of formula (XII)

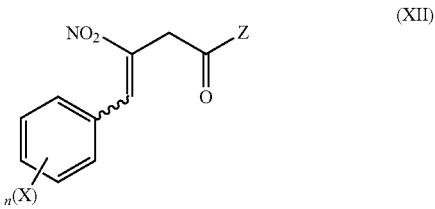

wherein and X, n, and Z are the same as above.

In another optional embodiment steps (l), (m) and (n) of the option (F) are replaced by (s) reduction of the benzylic hydroxy group of compound of formula (X)

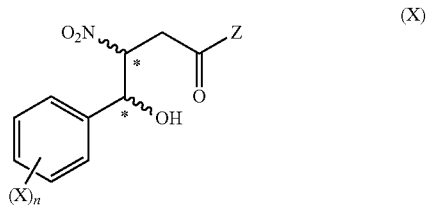

wherein the stereogenic centers marked with an * are either in (R)- or (S)-configuration at marked center, and X, n and Z are the same as above, by treating with silicon hydrides such as triethylsilane, or by catalytic hydrogenation on precious metal catalyst, or by transformation of the compound (X) to ester (XI) according to step (l) and catalytic hydrogenation of the ester to give the compound (XIII)

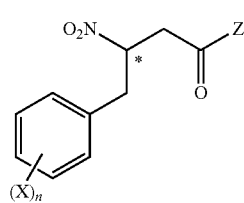

(XIII)

wherein the stereogenic center marked with an * is either in (R)- or (S)-configuration at marked center, or it is in racemic form, and X, n, and Z are the same as above.

In a special embodiment of the option (A) the saturation of the double bond (step (f)) is carried out in a chiral environment. Thus, the compound of formula (VIII)

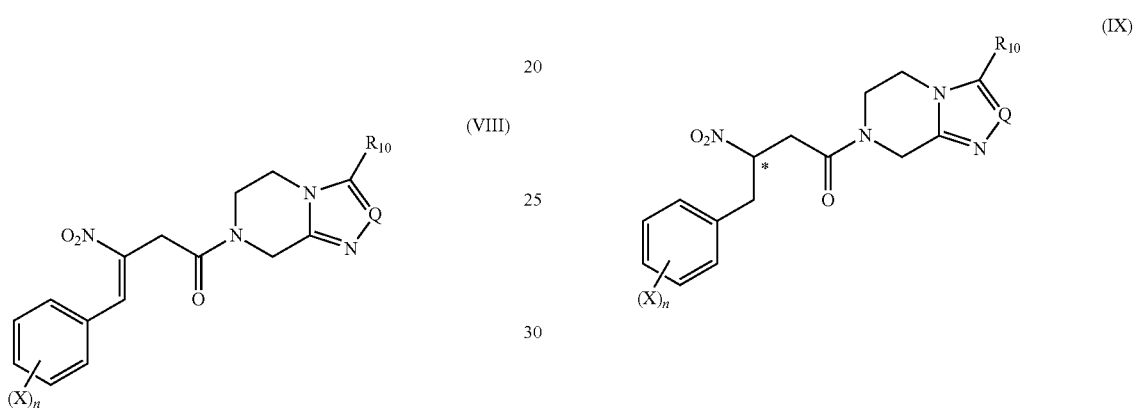

wherein X is halogen selected from fluoro, chloro or bromo, preferably fluoro, same or different, n is 1-4, Q is N, CH, C—$CF_3$, or C-phenyl, preferably N, and $R_{10}$ is H, $C_1$-$C_4$-alkyl or fluorinated $C_1$-$C_2$-alkyl, preferably trifluoromethyl, is treated by hydrogenation in the presence of transition metal preferably selected from rhodium, iridium or ruthenium and in the presence of chiral ligands selected from phosphines, diphosphines such as BINAP or amine-amide ligands such as (S,S)—N-(2-amino-1,2-diphenylethyl)methanesulfonamide to give a compound of formula (IX)

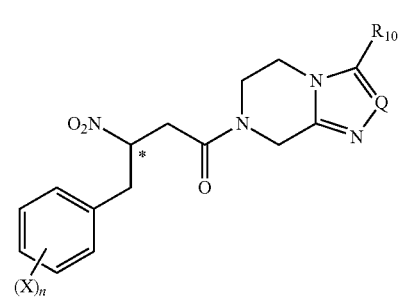

(IX)

wherein X, n, Q and $R_{10}$ are the same as above and the configuration on stereogenic center marked with an * is enriched in (R)- or (S)-configuration, preferably is enriched over 30% e.e., more preferably to over 60% e.e., most preferably to over 90% e.e.

In another option of enantioselective double bond saturation the compound of formula (VIII) can be subjected to biological reduction by reducatases of various microorganisms preferably selected from the group *Actinomyces, Saccharomyces* (using baker's yeast) or Bacteria genus *Clostridium.*

In a preferred option for preparation of DPP-4 inhibitors the compound of formula (IX) is enriched in (R)-enantiomer more preferably to over 60% e.e., more preferably to over 90% e.e. most preferably to over 97% e. e.

In a special preferred option for preparation of DPP-4 inhibitors of formula (IX)

wherein X, n, Q and $R_{10}$ are the same as above and the stereogenic center marked with an * is either in (R)- or (S)-configuration at marked center is enriched in (R)-enantiomer by separation of enantiomers using preparative chiral column chromatography.

In a preferred option the separated (S)-enantiomer is subsequently further racemized. In more preferred option the (R)-enantiomer and (S)-enantiomer in racemic mixture are further separated using said chromatography. Racemized mixtures can be enantiomerically separated in cycles for high yield enantiomeric enrichment of the desired (R)-enantiomer of the compound of the formula (IX).

In the most preferred option for preparation of DPP-4 inhibitors the compound of formula (IX) is enriched in (R)-enantiomer having over 60% e.e., preferably over 90% e.e., more preferably over 95% e.e, most preferably over 99% e.e.

In a special embodiment of the invention the method is used for the preparation of sitagliptin. In a preferred embodiment the option (A) is used and the substituents in formulas (I) to (IX) have the following meaning n is 3

X is fluoro in positions 2, 4 and 5 of benzene ring as regards to the side chain Y is N R is trifluoromethyl.

An illustrative and preferred but not limited approach of this special embodiment is shown in Scheme 5 and described in further detail as a representative embodiment below.

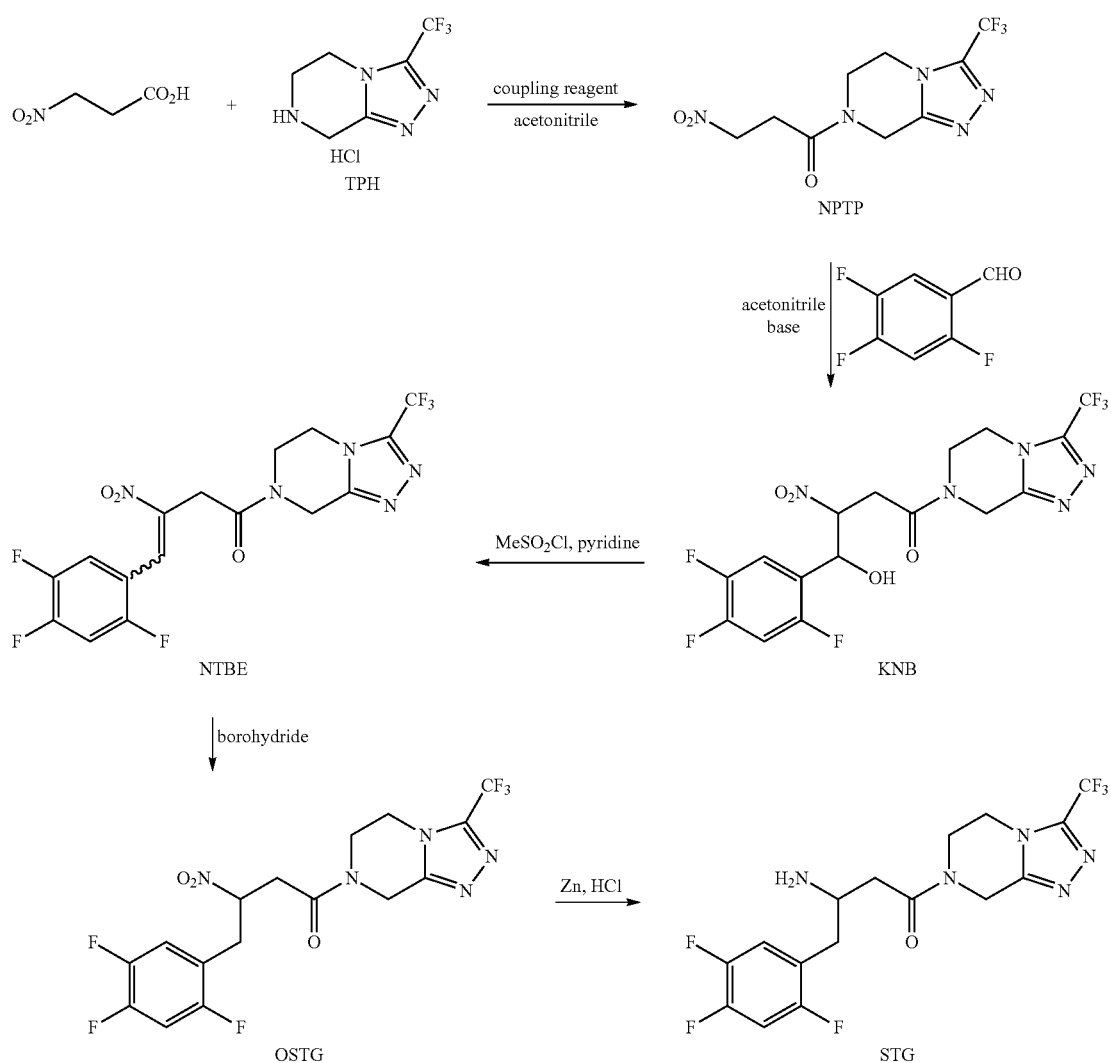

Scheme 5

In the first step of the embodiment 3-nitropropionic acid is coupled with TPH (compound (IIIa) with R=CF$_3$, Y=N) in an aprotic solvent selected from halogenated aliphatic hydrocarbons, aromatic hydrocarbons, ethers or nitriles or mixture thereof, preferably in acetonitrile by means of coupling reagents such as thionyl chloride, oxalyl chloride, activated isoureas, or carbodiimides, preferably N-(3-dimethylaminopropyl)-N'-ethylcarbodiimide hydrochloride in 0-50%, preferably 5-20% molar excess, optionally in the presence of bases preferably selected from tertiary amines, such as, triethylamine, ethyldiisopropylamine or N-methylmorpholine to give NPTP (compound of formula (IV) with R$_{10}$=CF$_3$, Y=N), which is isolated after reducing of volume of solvent, extraction from alkaline water/water immiscible solvent biphasic system and precipitation of concentrated organic solvent solution with ethers, preferably methyl t-butyl ether.

In the next step of the embodiment NPTP is coupled with 2,4,5-trifluorobenzaldehyde (compound of formula (V) with (X)$_n$ being 2,4,5-trifluoro) in the presence of a base in a polar protic or aprotic solvent, selected from water, alcohols, amides, sulfoxides, sulphones or nitriles, preferably in dry acetonitrile at 0-50° C., preferably at room temperature for 5-48 h, preferably for 15-25 h. Any base selected from amides, hydrides, hydroxides, amidines, tertiary amines can be used, but the preferred base is selected from inorganic basic salts, such as acetates, carbonates, phosphates, most preferably potassium phosphate tribasic in catalytic submolar amounts, preferably in 5-20% molar amount is used. The product KNB (compound of formula (VI) with (X)$_n$ being 2,4,5-trifluoro, R$_{10}$=CF$_3$, Y=N) is isolated after reducing the reaction solvent and treating with water/chlorinated solvent mixture as a solid mixture of four isomers.

In the next step of the embodiment KNB is treated with a sulfonyl chloride or anhydride selected from methanesulfonyl chloride, p-toluenesulfonyl chloride or trifluoromethanesulfonyl anhydride, preferably with methanesulfonyl chloride in 1-3 fold molar excess in the presence of a base selected from tertiary amines or basic heterocycles, preferably in the presence of pyridine. The reaction is carried out in an inert solvent selected from nitriles, esters or chlorinated hydrocarbons, aromatic hydrocarbons, or without solvent in the presence of base in high excess, preferably in pyridine at 0-50° C., preferably at room temperature for 1-10 h. The product NTBE (compound of formula (VIII) with (X)$_n$ being 2,4,5- trifluoro, $R_{10}=CF_3$, $Y=N$) is isolated after purification as a solid powder in (E) and/or (Z) configuration.

In the next step of the embodiment NTBE is reduced by catalytic hydrogenation using iridium, rhodium or ruthenium complexes in the presence of molecular hydrogen or hydrogen donors or in the presence of hydrides, preferably it is reduced by aluminium or boron hydrides. In a most preferred example sodium borohydride in $C_1$-$C_4$-alcohol, preferably isopropanol is used and the reaction is carried out at 0-50° C., preferably at room temperature for 1-10 h. The racemic product OSTG (compound of formula (IX) with $(X)_n$ being 2,4,5-trifluoro, $R_{10}=CF_3$, $Y=N$) is isolated after the removal of inorganic salt by water/organic solvent extraction and chemical purification as a solid powder.

The racemic product OSTG is separated to (R) and/or (S) enantiomer by preparative chiral chromatography using chiral supporters. Preferably supporters are selected from commercially available stationary phases, more preferably from supporters of classical (non-RP) type, furthermore preferably from amylose derivatised silicas, most preferably from stationary phases listed in Table 1. The mobile phases are preferably selected from organic solvents or mixtures of organic solvents, most preferably from mixtures of $C_1$-$C_4$-alcohols and $C_5$-$C_{10}$ alkane or fluorinated alkanes, in which preferable alcohols are methanol, ethanol, propanol or isopropanol, and most preferable alkanes are n-hexane, n-heptane or isooctane. The temperatures employed in the described procedures are in the range from 5 to 40° C.

TABLE 1

Most preferable chiral stationary phases for separation OSTG enantiomers

| Chiral stationary phase | Commercial name |
| --- | --- |
| Amylose tris (3,5-dimethylphenylcarbamate) immobilized on a silica support | CHIRALPAK ® IA |

TABLE 1-continued

Most preferable chiral stationary phases for separation OSTG enantiomers

| Chiral stationary phase | Commercial name |
| --- | --- |
| Amylose tris (3,5-dimethylphenylcarbamate) coated on a silica support | CHIRALPAK ® AD |
| Amylose tris [(S)-alfa-methylbenzylcarbamate) coated on a silica support | CHIRALPAK ® AS |

Chromatographic conditions are preferably selected to separate (R) and/or (S) enantiomer, preferably (R)-OSTG, in yield of over 30% of pure enantiomer, more preferably over 60%, most preferably over 90%, wherein pure enantiomer means having over 60% e.e., preferably over 90% e.e., more preferably over 95% e.e, most preferably over 99% e.e. In the synthesis of sitagliptin enantiomerically pure fractions of (R)-OSTG are collected, evaporated to the concentration suitable for further conversion or to get a solid pure compound.

It was further surprisingly found that OSTG enantiomers can racemise in a technically suitable time in the presence of mixture of an acid and a base. An undesired enantiomer of OSTG e.g. derived by achiral syntheses or as side products of enantioselective separation can thus be re-utilized by racemisation diminishing the unfavorable consequence of a loss of at least 50% of the produced material. Cycles of separation and racemisation allow high yield preparation of one enantiomer, preferably the (R)-enantiomer, of OSTG in a technically suitable and economically desirable manner.

An illustrative and preferred but not limited approach of this special embodiment is shown in Scheme 6 and described in further detail as a representative embodiment below, which is not intended to limit the scope of the invention to the shown embodiment.

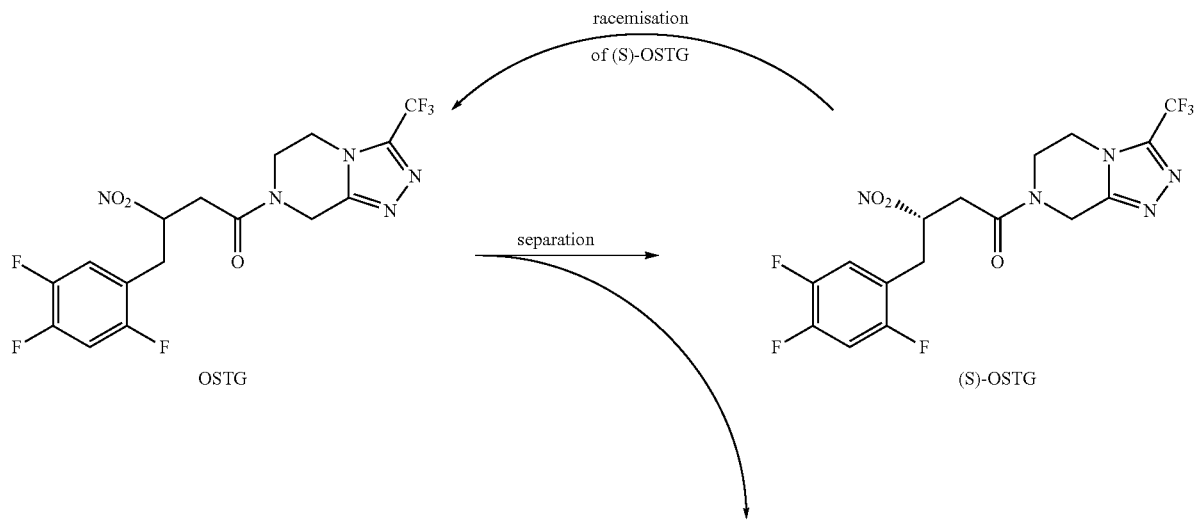

Scheme 6

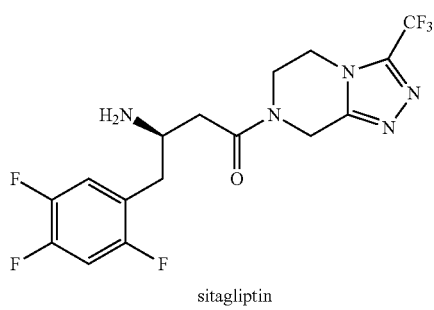

sitagliptin

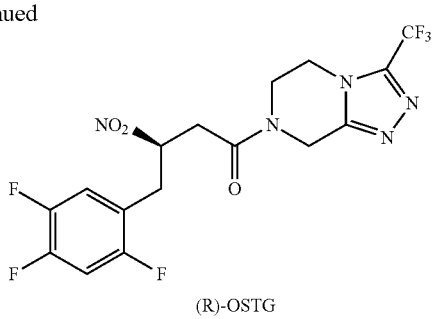

(R)-OSTG further conversion ←

The efficiency of racemisation of the acid/base mixture is considerably higher than in acid or base alone. Preferably the acid is used in excess to base, most preferably 2 to 3 equivalents of acid in respect to base are used. Amount of base in respect to OSTG is from 0.01 to 100 equivalents, more preferably the amount of base used is in the range of 0.5 to 5 equivalents, most preferably the amount of base is in the range of 1-3 equivalents.

Acid is selected from inorganic or organic acid or the mixture of the two, preferably the acid is selected from organic acid, more preferably acid is selected from $C_1$-$C_4$ organic acid, most preferably acid is acetic acid.

The base is selected from inorganic or organic base or the mixture of the two, preferably the base is selected from organic bases, more preferably the base is selected from the group of tri-$C_1$-$C_6$-alkylamine, the most preferable base is triethylamine.

The reaction is optionally carried out in the absence or presence of a diluting solvent. The diluting solvent is preferably selected from a group of polar solvents, selected from amides, sulfoxides, nitriles ketones or alcohols, more preferably from $C_1$-$C_6$ alcohols, most preferably the reaction medium is diluted by methanol. Reaction is carried out at from 0 to 200° C., preferably reaction is carried out at from 25 to 150° C., most preferably reaction is carried out at from 40 to 100° C. The technically reasonable time is between 1 min to 1 week, preferably the reaction time is between 15 minutes and 24 hours, most preferably reaction time is between 1 and 8 hours. The extent of the racemisation in a technically reasonable time is at least 60% (to give the ratio of isomers 30:70), preferably at least 80% (40:60), most preferably at least 90% (45:55).

The racemised mixture of OSTG is finally isolated by routine methods and submitted to the new chiral separation by chromatography as an independent batch or is joined to the racemate prepared by the main synthetic procedure. Using several cycles of separation/racemisation process the yield is enhanced from 35-45% in one cycle to at least 70% of enantiomerically pure (R)-OSTG.

In another embodiment of preparation of an enantiomer of OSTG, preferably (R)-OSTG, is enantioselective reduction of the double bond. NTBE is therefore reduced by catalytic hydrogenation using transition metal and at least one chiral ligand, preferably it is reduced by rhodium with diphosphine ligand. In a most preferred example rhodium complex with (S)-(−)-(1,1'-binaphthalene-2,2'-diyl)bis(diphenylphosphine) under 10-100 bar of hydrogen, preferably 50 bar of hydrogen is used and the reaction is carried out at 0-70° C., preferably at 50° C. for 1-20 hours. The enantiomerically enriched product OSTG (compound of formula (IX) with $(X)_n$ being 2,4,5-trifluoro, $R_{10}$=$CF_3$, Y=N) is isolated after the removal of inorganic salt by water/organic solvent extraction and chemical purification as a solid powder. Product can be further enantiomerically enriched by crystallization or by preparative chiral column chromatography to pure (R) and (S)-enantiomer of OSTG.

In the last step of this embodiment the nitro group in OSTG is reduced. The preferred methods use cheap inorganic reducing agents selected from inorganic sulfides, low-valent metal salts or elemental metal in the presence of acids. The most preferred method of transformation of OSTG to STG (compound of formula (I) with $(X)_n$ being 2,4,5-trifluoro, $R_{10}$=$CF_3$, Y=N) is a reduction with zinc and hydrochloric acid in $C_1$-$C_4$-alcohol, preferably methanol at 0-50° C., preferably at room temperature for 15 min to 24 hours, preferably for 1 to 8 hours.

In an analogous way (R)-OSTG is reduced to sitagliptin (compound (R)-STG), which is isolated as oil that slowly solidifies. Sitagliptin can then be further transformed to a pharmaceutically acceptable salt, preferably to phosphate, for example by treating an alcohol solution of sitagliptin base with the corresponding acid of the desired salt, such as with ortho-phosphoric acid.

Alternative and variable synthetic ways to obtain other β-amino acid derivatives and in particular other β-aminobutyryl compounds having γ-phenyl and/or heterocyclic structural moieties become apparent from the description of the embodiments and illustrations above.

In a further aspect the present invention provides key intermediate compounds useful for synthesizing gliptins (dipeptidyl peptidase-4 (DPP-4) inhibitors) as particular β-aminobutyryl compounds having γ-phenyl and/or heterocyclic structural moieties.

In another aspect, the present invention provides a pharmaceutical composition for administering a therapeutically effective amount of a gliptin compound, notably sitagliptin and more preferably its phosphate salt, as produced according to the present invention in unit dosage form with one or more pharmaceutically acceptable carriers or other excipients. A therapeutically effective amount of sitagliptin salt of the present invention is amount of salt ranging, when calculated as sitagliptin base, from 5 to 200 mg, preferably from 10 to 150 mg, more preferably from 25 to 100 mg.

Sitagliptin, preferably its phosphate salt, prepared according to the present invention can be embodied for example in form of tablet, capsules, pellets, granules and suppositories or their combined forms. Pharmaceutical composition in accordance with present invention can be suitable for immediate release or modified release of sitagliptin salts of the present invention. Solid pharmaceutical compositions can be for example coated with aim of increasing peletibility or regulating the disintegration or absorption.

Pharmaceutically acceptable excipients may be selected from the group consisting of binders, diluents, disintegrating agents, stabilizing agents, preservatives, lubricants, fragrances, flavoring agents, sweeteners and other excipients known in the field of the pharmaceutical technology. Preferably, carriers and excipients may be selected from the group consisting of lactose, microcrystalline cellulose, cellulose derivatives, (e.g. hydroxypropylcellulose, croscarmellose sodium), polyacrylates, calcium carbonate, starch, colloidal silicone dioxide, anhydrous dibasic calcium phosphate, sodium starch glycolate, talc, magnesium stearate, sodium stearyl fumarate, mannitol, polyvinylpyrrolidone, polyethylene glycol and other excipients known in the field of the pharmaceutical technology.

Optionally, the pharmaceutical compositions of the invention may be combination products comprising one or more additional pharmaceutically active components in addition to sitagliptin phosphate according to the present invention, preferably one or more additional pharmaceutically active components are selected from the group consisting of insulin sensitizers, insulin, insulin mimetics, sulfonylureas, α-glucosidase inhibitors, glucagon receptor antagonists, GLP-1, GLP-1 analogues, GLP-1 mimetics, GLP-1 receptor agonists, GIP, GIP mimetics, PACAP, PACAP mimetics, PACAP receptor agonists, cholesterol lowering agents, PPARδ agonists, antiobesity compounds, ileal bile acid tranporter inhibitors, agents intended for use in inflammatory conditions, antihypertensive agents, glucokinase activators (GKAs), inhibitors of 11β-hydroxysteroid dehydrogenase type 1, inhibitors of cholesteryl ester transfer protein (CETP) and inhibitors of fructose 1,6-bisphosphatase.

Most preferably additional pharmaceutically active component is metformin and/or its pharmaceutically acceptable salt.

The pharmaceutical compositions according to the present invention may be prepared by methods known in the field of the pharmaceutical technology.

A further aspect of the present invention is a method for treatment and/or prevention in mammal of clinical conditions for which DPP-IV inhibitor is indicated, in particular treatment of Type 2 diabetes, hyperglycemia, insulin resistance, and obesity, with a medicament by using an effective amount of sitagliptin phosphate according to the present invention.

Another aspect the present invention is related to use of sitagliptin, preferably its phosphate salt, prepared according to the present invention for the manufacture of medicament for treatment and/or prevention in mammal of clinical conditions for which DPP-IV inhibitor is indicated, in particular treatment of type 2 diabetes, hyperglycemia, insulin resistance, and obesity.

The following examples illustrate the present invention and are not intended to limit the scope of the invention.

Example 1

3-nitro-1-(3-(trifluoromethyl)-5,6-dihydro-[1,2,4] triazolo[4,3-a]pyrazin-7(8H)-yl)propan-1-one (NPTP)

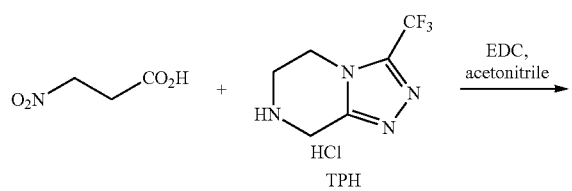

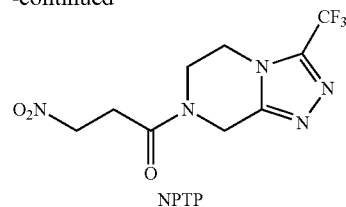

The title compound was prepared using the method described in WO 2008/040974.

A mixture of 3-nitropropionic acid (20.0 g, 0.168 mol), 3-(trifluoromethyl)-5,6,7,8-tetrahydro-[1,2,4]triazolo[4,3-a]pyrazine hydrochloride (48.0 g, 0.21 mol) in acetonitrile (400 mL) is cooled to 0° C. and 4-methylmorpholine (16.9 g, 0.168 mol) is added, followed by N-(3-dimethylaminopropyl)-N'-ethylcarbodiimide hydrochloride (EDC) (48.4 g, 0.25 mol) after 5 min. The resulting mixture is stirred at room temperature for 20 hours. The resulting mixture is concentrated to about ⅔ of its volume and ethyl acetate is added (750 mL). The resulting mixture is washed twice with water (200+100 mL), sat. aq. sodium hydrogencarbonate (200 mL), brine (200 mL) and dried with sodium sulfate. The resulting clear solution is concentrated under reduced volume and MTBE is added (100 mL). The precipitated white solid is filtered off, washed with MTBE (200 mL) and dried under reduced pressure to yield 38.8 g (79% yield) of NTPT as white powder.

Example 2

4-hydroxy-3-nitro-1-(3-(trifluoromethyl)-5,6-dihydro-[1,2,4]triazolo[4,3-a]pyrazin-7(8H)-yl)-4-(2,4,5-trifluorophenyl)butan-1-one (KNB)

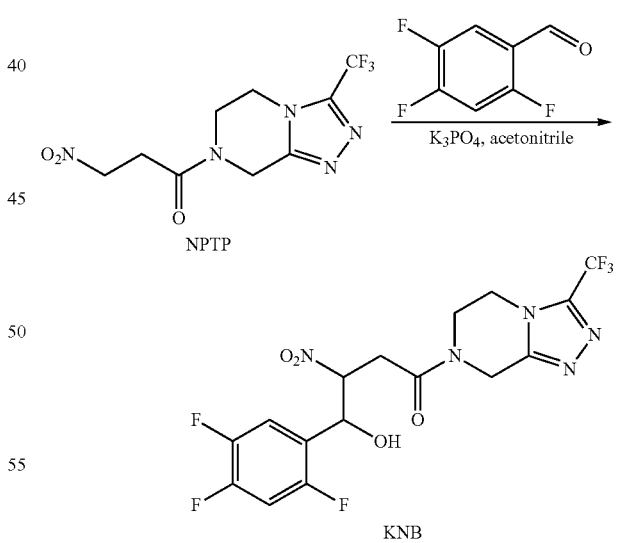

To a mixture of NPTP (29.3 g, 100 mmol), potassium phosphate tribasic (1.54 g, 7.3 mmol) and dry acetonitrile (135 mL) is added 2,4,5-trifluorobenzaldehyde (11.4 mL, 100 mmol) and the resulting mixture is stirred at room temperature for 20 hours. The resulting mixture is concentrated under reduced pressure and water (500 mL) and dichloromethane (50 mL) are added. The mixture is cooled to 0° C. and stirred at this temperature for 1 hour. During this period a white precipitate is formed, which is filtered off and washed with cold water (100 mL) followed by cold dichloromethane (100 mL) to yield 30.9 g (68% yield) of KNB as white powder. From filtrate another fraction precipitates out, which is also filtered off and washed with cold water (100 mL) followed by cold dichloromethane (100 mL) to yield 4.1 g (9% yield) of KNB as white powder. Both fractions are combined to yield a total of 35 g (77% yield) of KNB as mixture of diastereoisomers. First diastereoisomer: $^1$H NMR (DMSO-D6): δ 2.67 (m, 1H), 3.47 (m, 1H), 3.70 (m, 0.5H), 3.90-4.27 (m, 3.5H), 4.66-5.15 (m, 3H), 5.49 (s, 1H), 6.62 (m, 1H), 7.51-7.70 (m, 2H). Second diastereoisomer: $^1$H NMR (DMSO-D6): δ 3.01 (m, 1H), 3.20 (m, 0.5H), 3.44 (m, 1H), 3.80 (m, 0.5H), 3.88-4.32 (m, 4H), 4.74 (m, 1H), 4.86-5.02 (m, 2H), 5.11-5.28 (m, 2H), 6.56 (m, 1H), 7.47-7.62 (m, 2H). HPLC-MS (ES, m/z): 454 [M+H]$^+$.

Example 3

3-nitro-1-(3-(trifluoromethyl)-5,6-dihydro-[1,2,4] triazolo[4,3-a]pyrazin-7(8H)-yl)-4-(2,4,5-trifluorophenyl)but-3-en-1-one (NTBE)

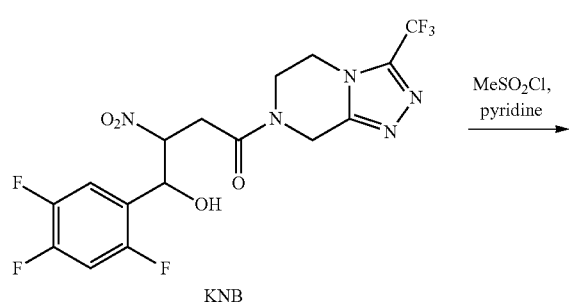

KNB

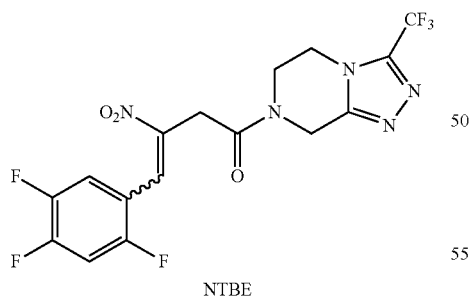

NTBE

To a solution of KNB (45.3 g, 100 mmol) in pyridine (200 mL) is added methanesulfonyl chloride (25.4 g, 222 mmol) and the resulting mixture is stirred at room temperature for 4 hours. The solution is cooled to 0° C. and water (5 mL) is added, followed by CELITE® (diatomite filter) (100 g). Pyridine is removed under reduced pressure and the resulting mixture is subjected to chromatography (silica gel; hexane; ethyl acetate=50:50→0:100) to give 29.5 g (68% yield) of NTBE as yellowish powder. $^1$H NMR (DMSO-D6): δ 3.98 (m, 1H), 4.05-4.17 (m, 4H), 4.28 (m, 1H), 4.92 (s, 1H), 5.12 (s, 1H), 7.63-7.79 (m, 2H), 7.10 (m, 1H). HPLC-MS (ES, m/z): 436 [M+H]$^+$.

Example 4

3-nitro-1-(3-(trifluoromethyl)-5,6-dihydro-[1,2,4] triazolo[4,3-a]pyrazin-7(8H)-yl)-4-(2,4,5-trifluorophenyl)but-3-en-1-one (NTBE)

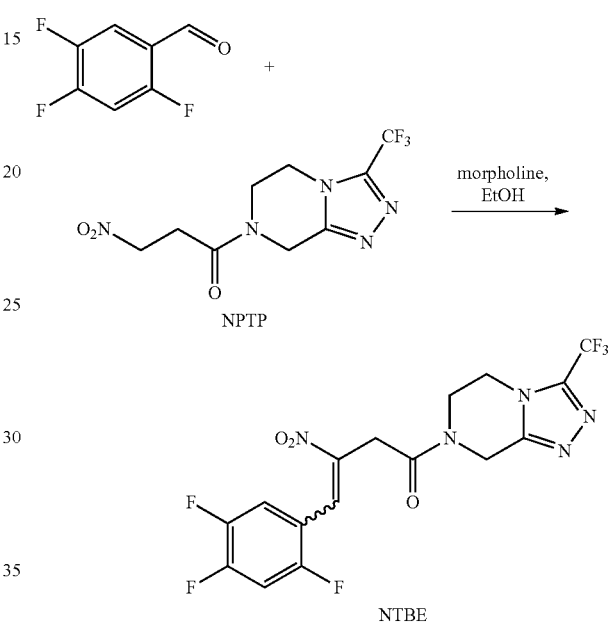

A mixture of NPTP (1.17 g, 4 mmol), 2,4,5-trifluorobenzaldehyde (0.64 g, 4 mmol), morpholine (0.20 mL, 2.3 mmol) and ethanol (4 mL) is refluxed for 3 h and concentrated. The resulting oil is subjected to chromatography (silica gel; toluene:ethyl acetate=80:20→50:50) to give 0.25 g (14% yield) of NTBE as yellow powder.

Example 5

3-nitro-1-(3-(trifluoromethyl)-5,6-dihydro-[1,2,4] triazolo[4,3-a]pyrazin-7(8H)-yl)-4-(2,4,5-trifluorophenyl)butan-1-one (OSTG)

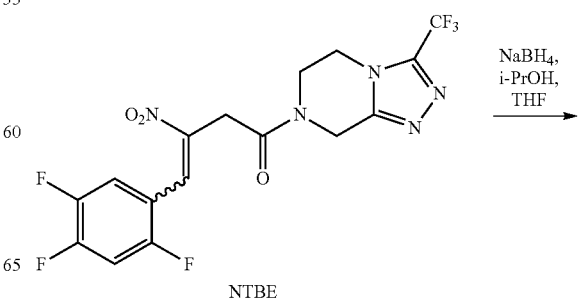

NTBE

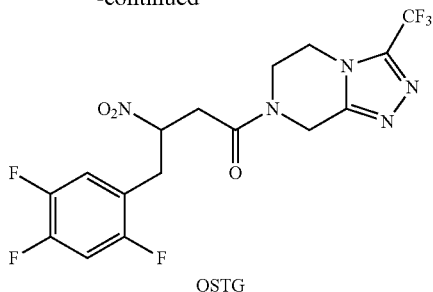

OSTG

To a cold (0° C.) solution of NTBE (2.17 g, 5 mmol) in a mixture of 2-propanol (5 mL) and tetrahydrofurane (10 mL) is added sodium borohydride (227 mg, 6 mmol) and the resulting mixture is stirred for 3 hours. To the resulting mixture is added 40% aqueous phosphoric acid (5 mL) and water. The organic solvents are removed under reduced pressure and dichloromethane (20 mL) is added, followed by 1 M aqueous sodium hydroxide so that the pH is 8. The organic phase is dried over sodium sulfate and concentrated under reduced pressure. The resulting white powder is washed with a mixture of ethyl acetate/hexane 1:1 (v/v) (25 mL) and dried under reduced pressure to give 0.84 g (39% yield) of racemic OSTG as white powder. $^1$H NMR (DMSO-D6): δ 3.07-3.28 (m, 3H), 3.35-3.47 (m, 1H), 3.78-4.19 (m, 3H), 4.21-4.34 (m, 1H), 4.71-5.18 (m, 3H), 7.47-7.62 (m, 2H). HPLC-MS (ES, m/z): 438 $[M+H]^+$.

Example 6

3-amino-1-(3-(trifluoromethyl)-5,6-dihydro-[1,2,4]triazolo[4,3-a]pyrazin-7(8H)-yl)-4-(2,4,5-trifluorophenyl)butan-1-one (STG)

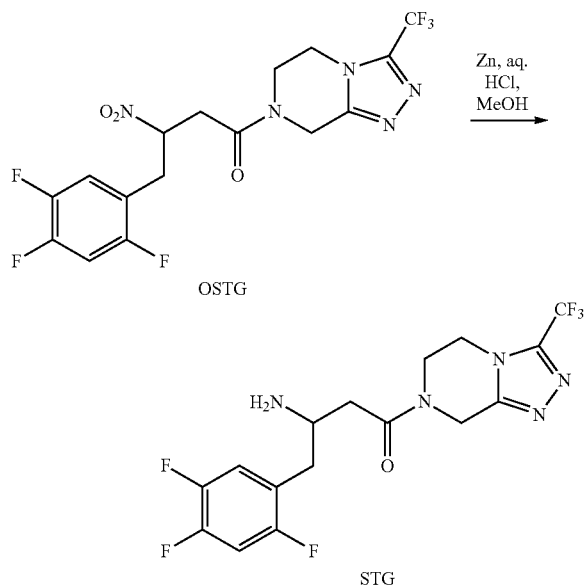

To a mixture of OSTG (0.11 g, 0.25 mmol), powdered zinc (0.12 g) and methanol (2 mL) is added drop wise a 37% aqueous HCl and the mixture is stirred at room temperature for 30 min. Zinc is removed by filtration and the resulting clear solution is concentrated under reduced pressure. To the remaining oil is added water (5 mL), followed by 1 M aqueous sodium hydroxide so that the pH is 10 and the product is extracted with dichloromethane (3×10 mL). The organic phases are combined, dried over sodium sulfate and concentrated under reduced pressure to give 95 mg (93% yield) of STG as yellowish oil.

Example 7

Sitagliptin Phosphate

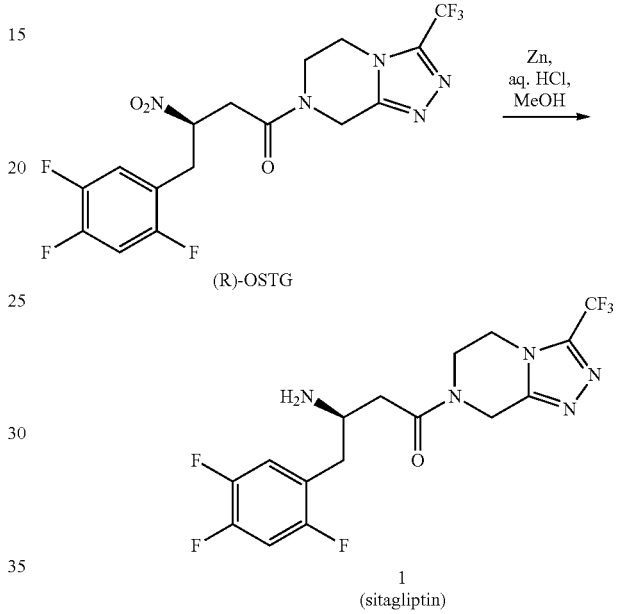

To a mixture of (R)-OSTG (0.11 g, 0.25 mmol), powdered zinc (0.12 g) and methanol (2 mL) is added drop wise a 37% aqueous HCl and the mixture is stirred at room temperature for 30 min. Zinc is removed by filtration and the resulting clear solution is concentrated under reduced pressure. To the remaining oil is added water (5 mL), followed by 1 M aqueous sodium hydroxide so that the pH is 10 and the product is extracted with dichloromethane (3×10 mL). The organic phases are combined, dried with sodium sulfate and concentrated under reduced pressure to give 89 mg (87% yield) of sitagliptin base as glassy solid.

The free base of 1 is dissolved in 1 mL of ethanol followed by the addition of 0.05 g 85% ortho-phosphoric acid. The resulting suspension is cooled for 15 min at 0° C. and filtered. The product is washed with 1 mL of ethanol and 2.5 mL of ether and dried on filter for 1 h. 85 mg of the off-white powdery product of sitagliptin phosphate is obtained.

Example 8

3-nitro-1-(3-(trifluoromethyl)-5,6-dihydro-[1,2,4]triazolo[4,3-a]pyrazin-7(8H)-yl)-4-(2,4,5-trifluorophenyl)butan-1-one (OSTG)

NTBE (0.1 mmol) and bis(1,5-cyclooctadiene)rhodium(I) tetrafluoroborate (0.004 mmol) are weighed in a flask under inert atmosphere. Methanol is added (3 mL), the reaction mixture is purged with nitrogen and hydrogen, then heated to 50° C., pressurized to 25 bar with hydrogen and stirred for 16 hours. HPLC analysis shows 90 area % of OSTG.

Example 9

3-nitro-1-(3-(trifluoromethyl)-5,6-dihydro-[1,2,4]triazolo[4,3-a]pyrazin-7(8H)-yl)-4-(2,4,5-trifluorophenyl)butan-1-one (OSTG)

NTBE (0.1 mmol) and dichloro(pentamethylcyclopentadienyl)rhodium(III) dimer (0.004 mmol) are weighed in a flask under inert atmosphere. Methanol is added (3 mL), the reaction mixture is purged with nitrogen and hydrogen, then heated to 50° C., pressurized to 25 bar with hydrogen and stirred for 16 hours. HPLC analysis shows 90 area % of OSTG.

Example 10

3-nitro-1-(3-(trifluoromethyl)-5,6-dihydro-[1,2,4]triazolo[4,3-a]pyrazin-7(8H)-yl)-4-(2,4,5-trifluorophenyl)butan-1-one (OSTG)

NTBE (0.1 mmol) and dichloro(pentamethylcyclopentadienyl)iridium(III) dimer (0.004 mmol) are weighed in a flask under inert atmosphere. Methanol is added (3 mL), the reaction mixture is purged with nitrogen and hydrogen, then heated to 50° C., pressurized to 25 bar with hydrogen and stirred for 16 hours. HPLC analysis shows 98 area % of OSTG.

Example 11

3-nitro-1-(3-(trifluoromethyl)-5,6-dihydro-[1,2,4]triazolo[4,3-a]pyrazin-7(8H)-yl)-4-(2,4,5-trifluorophenyl)butan-1-one (OSTG)

NTBE (0.1 mmol) and chloro[4-methyl-N-[(1R,2R)-2-[(S)-[[2-[(1,2,3,4,5-q)-2,3,4,5-tetramethyl-2,4-cyclopentadien-1-yl]phenyl]methyl]amino-κN]cyclohexyl]benzenesulfonamidato(2-)-κN]-rhodium (0.002 mmol) are weighed in a flask under inert atmosphere. Methanol is added (3 mL), the reaction mixture is purged with nitrogen and hydrogen, then heated to 50° C., pressurized to 25 bar with hydrogen and stirred for 16 hours. HPLC analysis shows 99 area % of OSTG and 11 enantiomeric excess.

Example 12

3-nitro-1-(3-trifluoromethyl)-5,6-dihydro-[1,2,4]triazolo[4,3-a]pyrazin-7(8H)-yl)-4-(2,4,5-trifluorophenyl)butan-1-one (OSTG)

NTBE (0.25 mmol) and [N-[(1S,2S)-2-(amino-κN)-1,2-diphenylethyl]methanesulfonamidato-κN]chloro[(1,2,3,4,5,6-η)-1,3,5-trimethylbenzene]-ruthenium (0.01 mmol) are weighed in a flask under inert atmosphere. Ethyl acetate (2.5 mL) and 5 M aqueous solution of sodium formate (2.5 mL) are added, the reaction is purged with argon and stirred at 65° C. for 3 hours. HPLC analysis shows 97 area % of OSTG and 35% enantiomeric excess.

Example 13

3-nitro-1-(3-trifluoromethyl)-5,6-dihydro-[1,2,4]triazolo[4,3-a]pyrazin-7(8H)-yl)-4-(2,4,5-trifluorophenyl)butan-1-one (OSTG)

Bicyclo[2.2.1]hepta-2,5-diene-rhodium(I) chloride dimer (0.00166 mmol) and (S)-(−)-(1,1'-binaphthalene-2,2'-diyl)bis(diphenylphosphine) (BINAP) (0.002 mmol) were stirred in dry and degassed DCE (0.12 mL) for 30 min at 45° C. under an argon atmosphere. After removal of the solvent under reduced pressure a solution of NTBE (0.041 mmol) in dry and degassed THF (0.200 ml) was added. Finally dry and degassed toluene (0.30 mL) was added. Argon was exchanged trough an hydrogen atmosphere and the solution was stirred at 50 bar and 50° C. for 16 h. HPLC analysis shows 79 area % of OSTG and 49% enantiomeric excess.

Example 14

Resolution of Enantiomers

Racemic OSTG was subjected to preparative chromatography using CHIRALPAK® AD as the stationary phase and heptane/ethanol 1:1 (v/v) as the mobile phase. The racemic OSTG was dissolved in methanol at concentration at least of 5 g/liter and injected to the column. The racemic mixture of OSTG were resolved and separated into enantiomers, typical retention time is 12 min for one (R)-OSTG and 18 for the other (S)-OSTG enantiomer. The chromatographic separation was carried out under the following conditions:

| | |
|---|---|
| Stationary phase: | CHIRALPAK ® AD, 20 μm particle size |
| Column length: | 250 × 50 mm |
| Temperature: | room temperature |
| Flow rate: | 120 ml/min |
| Detection: | UV 210 nm |
| Concentration: | 6.6 mg/ml |
| Injection volume: | 50 ml |
| Mobile phase: | n-heptane/Ethanol 50/50 |
| Retention time: | 30 minutes |

Eluated fractions were analysed to the contain of particular enantiomers, enantiomerically pure fractions or enantiomerically essentially pure fractions are collected and evaporated to get solid residues of (R)-OSTG and (S)-OSTG enantiomer.

Optional fractions which contain a mixture of both enantiomers or fractions which are too contaminated with the opposite enantiomer can be rechromatographated or combined with the unwanted isomer containing for regeneration.

This procedure is only a representative example, which does not limit variations in fractions collection, stationary and mobile phase in order to fit yields, chemical and enantiomerical purities to the most economical overall process, which produces a pharmaceutically acceptable product.

Example 15

Racemization of Enantiomerically Enriched OSTG

OSTG (50 mg, 13:87 ratio of enantiomers), formic acid (50 μL), triethylamine (11 μL) and 2-propanol (0.5 mL) were placed in a glass vial and stirred for 15 hours at 75° C. HPLC analysis revealed a mixture of enantiomers in 46:54 ratio.

Example 16

Racemization of Enantiomerically Enriched OSTG

OSTG (50 mg, 13:87 ratio of enantiomers), acetic acid (75 μL), triethylamine (11 μL) and 2-propanol (0.5 mL) were placed in a glass vial and stirred for 15 hours at 75° C. HPLC analysis revealed a mixture of enantiomers in 47:53 ratio.

Example 17

Preparation of OSTG

A mixture of N-tosylethylenediamine (13 mg) and dichloro(p-cymene)ruthenium(II) dimer (16 mg) in ethyl acetate (5 mL) was stirred at 60° C. for 15 minutes. To the obtained orange solution was added ethyl acetate (45 mL), NTBE (2.2 g) and 5 M aqueous sodium formate (10 mL). The resulting mixture was stirred at 60° C. for 3 hours and the phases were separated. The upper (organic) phase was concentrated to 90% of the initial volume and 2-propanol was added (25 mL). The mixture was again partially concentrated and 2-propanol was added (10 mL), cooled and the precipitated solid was filtered off and washed with 2-propanol to yield 1.77 g of racemic OSTG.

Example 18

Racemization of Enantiomerically Enriched OSTG

OSTG (150 mg, 11.5:88.5 ratio of enantiomers), acetic acid (225 μL), triethylamine (150 μL) and methanol (1.5 mL) were placed in a glass vial and stirred for 2 hours at 65° C. The reaction mixture was cooled down to 25° C., water (5.0 mL) was added and the reaction mixture was stirred for 10 minutes. Precipitated solid was filtered off, washed with water (2 mL) and dried to yield 120 mg of OSTG. HPLC analysis revealed a mixture of enantiomers in a 50:50 ratio.

Example 19

Preparation of Sitagliptine Phosphate from OSTG

A mixture of (R)-OSTG (0.20 g, obtained by chiral matrix chromatography) and zinc powder (1.0 g) in methanol (8 mL) was cooled to 0° C. and 36% aqueous hydrochloric acid (0.8 mL) was added during a period of 15 minutes. The resulting mixture is stirred at 25° C. for 5 hours and zinc was removed by decanting. To the resulting mixture was added water (15 mL) and methanol was removed under reduced pressure. The remaining aqueous solution was basified with aqueous ammonium hydroxide to pH 10 and the product was extracted with dichloromethane (3×25 mL). The combined organic phases were concentrated under reduced pressure and the residue dissolved in methanol (10 mL). The obtained mixture was filtered trough a short pad of silica gel (washing with methanol) and concentrated under reduced pressure. The obtained sitagliptin was dissolved in 2-propanol (2 mL) and 85% aqueous phosphoric acid (20 mL) was added while stirring. The precipitated solid was filtered off, washed with 2-propanol (2×0.6 mL) and dried to yield 0.14 g of sitagliptin phosphate.

The invention claimed is:

1. A process for an enrichment of one enantiomer of the compound of the formula (IX)

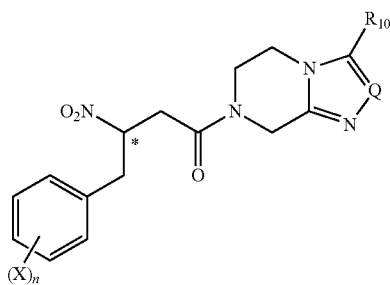

wherein the stereogenic center marked with an * either can be in (R)- or (S)-configuration at marked center; X is halogen selected from fluoro, chloro, or bromo, same or different, and n is 1-4, Q is N, CH, C—CF$_3$, or C-phenyl, and R$_{10}$ is H, C$_1$-C$_4$-alkyl or fluorinated C$_1$-C$_2$-alkyl, the process comprising providing a mixture of enantiomers of the compound of formula (IX); subjecting the mixture of enantiomers to chromatography so as to separate the enantiomers; collecting the separated enantiomers; subjecting a separated undesired enantiomer to a racemisation reaction wherein the racemisation of the separated undesired enantiomer is carried out in the presence of acid, base or a mixture of acid and base, wherein the acid is in molar excess in respect to the base and further wherein the acid is selected from C1-C4 carboxylic acids and the base is selected from tri-C1-C6 alkylamines.

2. The process according to claim 1, wherein the desired separated enantiomer of the compound of the formula (IX) is the (R)-enantiomer, and the undesired separated enantiomer of the compound of the formula (IX) is the (S)-enantiomer.

3. A compound defined by the following formula (IX)

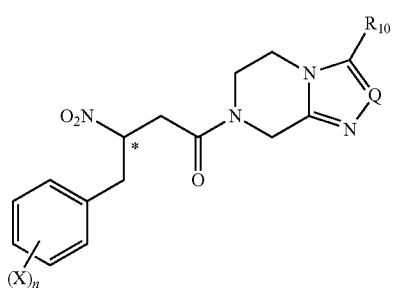

wherein the stereogenic centers marked with an * are either in (R)- or (S)-configuration at marked center; X is halogen selected from fluoro, chloro, or bromo same or different, and n is 1-4; Q is N, CH, C—CF$_3$, or C-phenyl; and R$_{10}$ is H, C$_1$-C$_4$-alkyl or fluorinated C$_1$-C$_2$-alkyl.

4. A process for an enrichment of one enantiomer of the compound of the formula (IX)

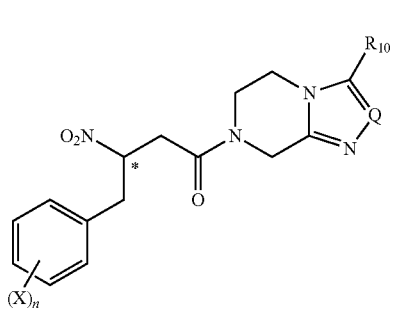

according to any one of claims 1-2, wherein the compound of the formula (IX) is prepared according to the process, comprising:

(i) providing a 2-nitropropionic acid derivative of formula (IIc)

(IIc)

wherein Z is (i-1) a substituent defined by the following compound of formula (III')

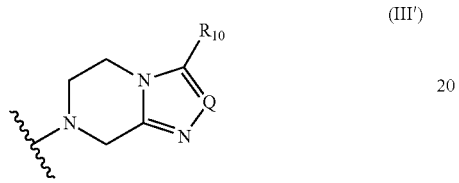
(III')

wherein Q is N, CH, C—$CF_3$, or C-phenyl, and $R_{10}$ is H, $C_1$-$C_4$-alkyl or fluorinated $C_1$-$C_2$-alkyl, preferably trifluoromethyl, or (i-2) OH, $OR^1$, $NR^2R^3$ or $OSiR^4R^5R^6$, wherein $R^1$ is $C_1$-$C_6$-alkyl or aryl-$C_1$-$C_2$-alkyl, $R^2$ is H, $C_1$-$C_4$-alkyl, arylmethyl, $C_1$-$C_4$-alkoxy or arylmethoxy, $R^3$ is H, $C_4$-alkyl or arylmethyl, and $R^4$, $R^5$ and $R^6$ independently are $C_1$-$C_4$-alkyl or phenyl, (ii) carrying out a coupling reaction by condensation of the 2-nitropropionic acid derivative of formula (11c) with an aldehyde of formula Ar—CHO in the presence of a base substance, wherein the aldehyde Ar—CHO is defined by formula (V)

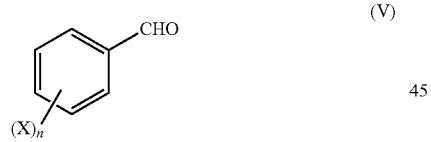
(V)

wherein X is halogen selected from fluoro, chloro, or bromo same or different, and n is 1-4, and obtaining a compound of formula (VIIIa) or (Via)

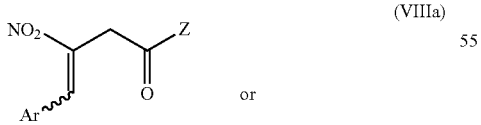
(VIIIa)

or

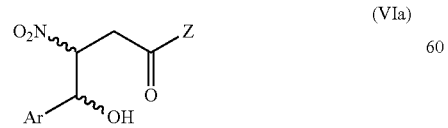
(VIa)

(iii-1) subjecting the compound of formula (VIIIa) or (VIa) to a conversion reaction to obtain a compound of formula (IXa)

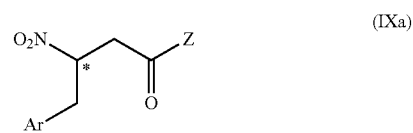
(IXa)

by a reaction selected from the group of esterification, dehydration, reduction, hydrogenation, elimination and combinations thereof, or (iii-2) subjecting the compound of formula (VIIIa) to a reduction reaction to obtain

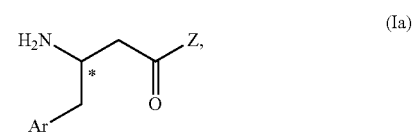
(Ia)

optionally forming a salt thereof;

wherein the stereogenic center marked with an * is either in (R)- or (S)-configuration at marked center, or it is in racemic form;

(iv) if Z optionally is as defined in (i-2), subjecting Z to structural modification, wherein the structural modification comprises steps of converting a compound of formula (XIIIa)

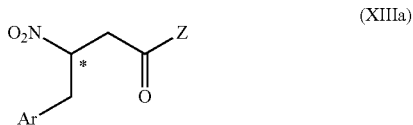
(XIIIa)

(if Z is other than OH) to compound of formula (XIVa),

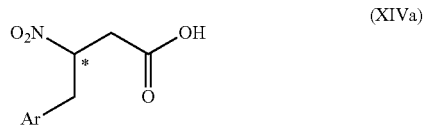
(XIVa)

activating the carboxylic group in the compound of formula (XIVa) and converting the activated derivative of formula (XIVa) to compound of formula (IXb)

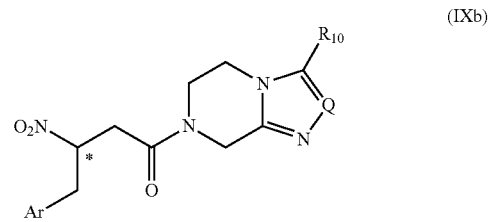
(IXb)

by reacting with compound of formula (III)

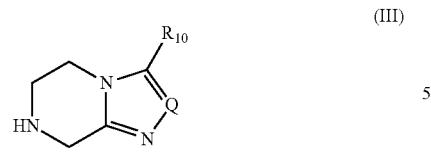 (III)
wherein Ar, *, Q and $R_{10}$ are as defined above yielding the compound (IX).
5. The process according to claim 4, wherein Q is N, CH, C—$CF_3$, or C-phenyl, preferably N, and $R_{10}$ is H, $C_1$-$C_4$-alkyl or fluorinated $C_1$-$C_2$-alkyl, which is trifluoromethyl.
* * * * *